US009464281B2

(12) United States Patent
Suda et al.

(10) Patent No.: US 9,464,281 B2
(45) Date of Patent: Oct. 11, 2016

(54) METHOD FOR CONCENTRATING VIRUSES, METHOD FOR CONCENTRATING CELLS OR BACTERIA, AND MAGNETIC COMPOSITE

(75) Inventors: Yasuo Suda, Kagoshima (JP); Masahiro Wakao, Kagoshima (JP); Takashi Kodama, Takarazuka (JP)

(73) Assignees: SUDx-Biotec Corporation, Kagoshima-shi (JP); National University Corporation Kagoshima University, Kagoshima-shi (JP); Neat Co., Ltd., Osaka-shi (JP)

( * ) Notice: Subject to any disclaimer, the term of this patent is extended or adjusted under 35 U.S.C. 154(b) by 152 days.

(21) Appl. No.: 12/844,742

(22) Filed: Jul. 27, 2010

(65) Prior Publication Data
US 2011/0027854 A1 Feb. 3, 2011

(30) Foreign Application Priority Data

Jul. 28, 2009 (JP) ................. 2009-175001
Mar. 2, 2010 (JP) ................. 2010-045753

(51) Int. Cl.
| | | |
|---|---|---|
| C12N 7/02 | (2006.01) | |
| G01N 33/566 | (2006.01) | |
| C12N 13/00 | (2006.01) | |
| B03C 1/01 | (2006.01) | |
| B03C 1/28 | (2006.01) | |
| B82Y 25/00 | (2011.01) | |
| C12N 1/20 | (2006.01) | |
| C12N 7/00 | (2006.01) | |
| C12Q 1/24 | (2006.01) | |
| G01N 33/543 | (2006.01) | |
| H01F 1/00 | (2006.01) | |

(52) U.S. Cl.
CPC ................. *C12N 13/00* (2013.01); *B03C 1/01* (2013.01); *B03C 1/288* (2013.01); *B82Y 25/00* (2013.01); *C12N 1/20* (2013.01); *C12N 7/00* (2013.01); *C12Q 1/24* (2013.01); *G01N 33/54326* (2013.01); *H01F 1/0054* (2013.01); *B03C 2201/18* (2013.01); *B03C 2201/26* (2013.01); *C12N 2760/16151* (2013.01)

(58) Field of Classification Search
None
See application file for complete search history.

(56) References Cited

U.S. PATENT DOCUMENTS

| | | | | |
|---|---|---|---|---|
| 5,447,859 | A * | 9/1995 | Prussak ......................... 435/239 | |
| 6,365,362 | B1 * | 4/2002 | Terstappen et al. ......... 435/7.23 | |
| 7,320,867 | B2 * | 1/2008 | Suda ............... A61K 47/48092 | |
| | | | | 435/137 |
| 2006/0104970 | A1 * | 5/2006 | Margel .................. A61K 31/00 | |
| | | | | 424/94.64 |
| 2007/0287195 | A1 | 12/2007 | Suda | |
| 2009/0136586 | A1 * | 5/2009 | Larm ..................... A61K 31/70 | |
| | | | | 424/529 |
| 2009/0176200 | A1 * | 7/2009 | Wakita ..................... C12N 7/00 | |
| | | | | 435/5 |
| 2009/0308814 | A1 * | 12/2009 | Colvin .................... B03C 1/015 | |
| | | | | 210/695 |
| 2011/0053250 | A1 | 3/2011 | Takakura et al. | |

FOREIGN PATENT DOCUMENTS

| | | |
|---|---|---|
| JP | 2009-148246 A | 7/2009 |
| JP | 2009-256261 A | 11/2009 |
| WO | 2005/077965 A1 | 8/2005 |
| WO | 2009/123348 A1 | 10/2009 |

OTHER PUBLICATIONS

"Orthomyxoviridae," Wikipedia.com (accessed Mar. 11, 2015).*
"Cytomegalovirus," Wikipedia.com (accessed Mar. 11, 2015).*
"Adenoviridae," Wikipedia.com (accessed Mar. 11, 2015).*
"Norovirus," Wikipedia.com (accessed Mar. 11, 2015).*
"Rotavirus," Wikipedia.com (accesed Mar. 11, 2015).*
"AdenoMag", Retrieved on Jul. 26, 2010, Web page Available at: http://www.ozbiosciences.com/adenomag.html.
"Development and Evaluation of Bio Diagnostic Agents, and Companies thereof", CMC Technical Library 146, CMC Publishing Co., Ltd., 2003, pp. 92-97, 109-113 of the document and 4 pages of partial English Translation.
"ViroMag & R/L", Retrieved on Jul. 26, 2010, Web page Available at: http://wvvw.ozbiosciences.conn/viromag.html.
Verreck et al., "Human IL-23-producing type 1 macrophages promote but IL-10-producing type 2 macrophages subvert immunity to (myco)bacteria", Proceedings of the National Academy of Sciences, vol. 101, No. 13, Mar. 30, 2004, pp. 4560-4565.
Sato et al., "High-sensitivity analysis of naturally occurring sugar chains, using a novel fluorescent linker molecule", The Journal of Biochemistry, vol. 146, No. 1, 2009, pp. 33-41.

(Continued)

*Primary Examiner* — Bradley L Sisson
(74) *Attorney, Agent, or Firm* — Morrison & Foerster LLP

(57) ABSTRACT

A method for concentrating viruses includes applying a magnetic force to a mixture containing: sugar chain-immobilized magnetic metal nano-particles each having a structure in which a sugar chain-immobilized metal nano-particle is bound to a first magnetic nano-particle; second magnetic particles with mean particle size larger than that of the sugar chain-immobilized magnetic metal nano-particles; and a specimen. Each sugar chain-immobilized metal nano-particle has a structure where a ligand-conjugate is bound to a metal nano-particle via sulfur atoms. The ligand-conjugate has a structure where a linker compound's amino group is connected to a sugar chain having a reducing terminal. The linker compound includes, in molecules thereof, an amino group, sulfur atoms, and a hydrocarbon chain having carbon-nitrogen bonds. This allows short-time concentration of viruses in a sufficient amount almost equal to that of centrifugation concentration, allowing safely and effectively concentrating target viruses, resulting in prompt, easy, and highly sensitive detection and identification of viruses.

3 Claims, 4 Drawing Sheets

(56) References Cited

OTHER PUBLICATIONS

Shimizu et al., "High-perfomiance affinity beads for identifying drug receptors", Nature Biotechnology, vol. 18, Aug. 2000, pp. 877-881.

Hanley et al., "Extracellular ATP induces oscillations of intracellular Ca2+ and membrane potential and promotes transcription of IL-6 in macrophages", Proceedings of the National Academy of Sciences, vol. 101, No. 25, Jun. 22, 2004, pp. 9479-9484.

Pflueger et al., "Preservation of cytotoxic function during multi-cycle immunomagnetic cell separations of human NK cells using a new type of magnetic bead", Journal of Immunological Methods, vol. 129, 1990, pp. 165-173.

Zhang, et al., "Classification and high sensitive detection of influenza Viruses based on their binding activity for sugar-chain", The 57th Annual Meeting of the Japanese Society for virology, 2009, 20 pages.

* cited by examiner

490μl of 0.5HAU
Influenza A Virus
Culture Solution

←—10μl of Solution 1

Solution 2 Left at
Room Temperature
for 30min

← Second Magnetic Body
Added or Not Added

← Apply Magnetic Force
by Neodymium Magnet

↗ 10000g, 10min

Precipitation  Supernatant          Precipitation  Supernatant

← Ultrapure Water 10μl           ← Ultrapure Water 10μl

Heat at 100°C                      Heat at 100°C
for 5min                           for 5min ← Apply Magnetic Force
by Neodymium Magnet ↗ 10000g, 10min Precipitation  Supernatant          Precipitation  Supernatant Real Time RT-PCR                   Real Time RT-PCR

FIG. 1

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 1
ttctaaccga ggtcgaaacg                                        20

<210> SEQ ID NO 2
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 2
acaaagcgtc tacgctgcag                                        20

<210> SEQ ID NO 3
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 3
ggactgcagc gtagacgctt                                        20

<210> SEQ ID NO 4
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 4
catyctgttg tatatgaggc ccat                                   24
```

METHOD FOR CONCENTRATING VIRUSES, METHOD FOR CONCENTRATING CELLS OR BACTERIA, AND MAGNETIC COMPOSITE

CROSS-REFERENCE TO RELATED APPLICATIONS

This Nonprovisional application claims priority under 35 U.S.C. §119(a) on Patent Applications No. 2009-175001 filed in Japan on Jul. 28, 2009 and No. 2010-045753 filed in Japan on Mar. 2, 2010, the entire contents of which are hereby incorporated by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 247322009100SequenceListing.txt, date recorded: Jul. 27, 2010, size: 2 KB).

FIELD OF THE INVENTION

The present invention relates to a new method for concentrating viruses, a new method for concentrating cells or bacteria, and to new magnetic composites. To be more specific, the present invention relates to: a method for concentrating viruses, capable of safely and efficiently concentrating viruses without centrifugation, by using a magnetic composite containing sugar chain-immobilized magnetic metal nano-particles and magnetic particles with a larger particle size than that of the nano-particles; a method for concentrating cells or bacteria, capable of safely, efficiently and selectively concentrating cells or bacteria without centrifugation, by using a magnetic composite containing protein-sugar chain-immobilized magnetic metal nano-particles and magnetic particles with a larger particle size than that of the nano-particles; and to the magnetic composite.

Identification of viruses that infect animals or plants and determination of their quantity are essential for diagnosis of infectious disease and for determination of a strategy for the treatment of the virus-derived diseases. However, the concentration of viruses existing in a living body (in a body fluid), foods, drinking water, river water etc. is not high enough, so there is a problem that a conventional diagnostic method cannot detect viruses in such small quantity, consequently. For example, since the concentration of influenza virus released from an infected person is less than the detection limit of the conventional simple examination kits or a PCR process at the initial stage of infection, it is difficult to detect influenza virus which will cause influenza disease.

The present invention allows safe, efficient, and selective concentration of viruses without troublesome centrifugation, by using sugar chain-immobilized magnetic metal nano-particles and second bigger-size magnetic particles based on the binding interaction between viruses and sugar chains. Further, the present invention allows safe, efficient, and selective concentration of cells or bacteria without troublesome centrifugation, by using protein-sugar chain-immobilized magnetic metal nano-particles and second bigger-size magnetic particles based on the binding interaction between antigen proteins on surfaces of the cells or bacteria and antibodies.

Accordingly, the present invention is applicable not only to analysis of functions of sugar chains and proteins, but also to highly sensitive detection of viruses, cells, or bacteria. Consequently, the present invention can contribute to developing new pharmaceuticals for viral diseases. Further, since the present invention also allows concentration of viruses or bacteria that infect domestic animals, agricultural products, or etc., the present invention allows predicting economical damage caused by those viruses or bacteria. In this manner, the present invention is widely applicable to pharmaceutical, biological and ecological industries.

BACKGROUND OF THE INVENTION

Most of the surfaces of our cells are covered with sugar chains. It is known that viruses recognize sugar chains existing on the surface of a cell, bind and migrate into cells, and infect the cells. The infection of viruses into higher animals or plants causes diseases. Often, the infectious viruses tend to infect the same species of animals or plants. For example, avian influenza viruses regularly do not infect human except for the case of the mutation of viral RNA. In cases of domestic animals, agricultural crops, and ornamental animals or plants, viruses that are capable of infecting such animals or plants are transmitted among the same species, causing damages in the production. Therefore, identification of viruses, bacteria etc. capable of infecting such animals or plants is essential for sensitive diagnosis, which contributes to the determination of the early treatment or prevention.

The inventors of the present invention have aimed to provide a method for concentrating target viruses etc. from a specimen containing a number of contaminants and for identifying the concentrated viruses in a short time, and have succeeded in developing a concentration method using sugar chain-immobilized metal nano-particles prepared by immobilizing to a metal a ligand-conjugate, in which a sugar chain is connected with the well-designed linker compound having a predetermined structure, and by using sugar chain linkages of viruses etc. (Japanese Patent Application Publication, Tokukai, No. 2009-148246 A (publication date: Jul. 9, 2009)) based on the binding interaction between sugar chains and viruses.

The size of viruses is approximately 100 nm, and recovery and concentration of viruses is generally carried out by high-speed centrifugation such as ultracentrifugation.

However, in the ultracentrifugation, an extremely large gravity has to be applied to a sample. Consequently, due to uneven balance in weight between samples, there would be a danger such as scattering of the samples. Since such scattering of samples must be avoided, there has been requested a method for concentrating viruses without using centrifugation. Similarly, also in a case of concentrating cells or bacteria, there has been requested a method for concentrating cells or bacteria without using centrifugation in order to avoid the aforementioned danger.

SUMMARY OF THE INVENTION

The present invention was developed in view of the foregoing problems. An object of the present invention is to provide a method for concentrating viruses, capable of concentrating viruses safely, efficiently and selectively without centrifugation, and a method for concentrating cells or bacteria, capable of concentrating cells or bacteria safely, efficiently and selectively without centrifugation.

The inventors of the present invention have diligently investigated methods that substitute for centrifugation, and found that magnetizing the sugar chain-immobilized metal nano-particles and collecting the sugar chain-immobilized metal nano-particles bound to viruses by a magnetic force exhibits collection efficiency almost equal to that in the case of centrifugation, and that such method allows safer concentration of viruses than the case of centrifugation. Thus, the inventors of the present invention have completed the present invention.

In one embodiment, a method for concentrating viruses includes the step of applying a magnetic force to a mixture containing (i) sugar chain-immobilized magnetic metal nano-particles having a structure in which a sugar chain-immobilized metal nano-particle is bound to a first magnetic nano-particles, (ii) second magnetic particles whose mean particle size is larger than that of the sugar chain-immobilized magnetic metal nano-particles, and (iii) a specimen, each of the sugar chain-immobilized metal nano-particles having a structure in which a ligand-conjugate is immobilized onto a metal nano-particle via sulfur atoms, the ligand-conjugate having a structure in which an amino group of a linker compound is connected to a sugar chain having a reducing terminal, and the linker compound including, in molecules thereof, an amino group, a sulfur atom, and a hydrocarbon chain having a carbon-nitrogen bond.

The inventors of the present invention have already produced sugar chain-immobilized magnetic metal nano-particles obtained by magnetizing sugar chain-immobilized metal nano-particles. The sugar chain-immobilized magnetic metal nano-particles possess a limited range of particle size and high water-dispersibility since sugar chains are immobilized onto the nano-particles in a stable state. Therefore, they are applicable to various fields such as life science, medical diagnosis, and biotechnology.

However, the magnetic force of the sugar chain-immobilized magnetic metal nano-particles was not sufficient. The inventors of the present invention have found that application of a magnetic force to the nano-particles did not allow sufficient concentration of viruses.

In order to solve this problem, the inventors of the present invention have diligently studied and found that the combined usage of the sugar chain-immobilized magnetic metal nano-particles with second magnetic particles whose mean particle size is larger than that of the sugar chain-immobilized magnetic metal nano-particles allows safe and effective concentration of viruses in a sufficient way almost equal to that in the case of centrifugation in a short time period.

As described above, the present invention is configured such that the sugar chain-immobilized magnetic metal nano-particles and second magnetic particles whose mean particle size is larger than that of the sugar chain-immobilized magnetic metal nano-particles are used in combination, and therefore the present invention allows short-time concentration of viruses in a sufficient way almost equal to that in the case of centrifugation. This allows concentrating target viruses safely and effectively, and allows prompt, easy, and highly sensitive detection and identification of viruses.

Magnetic composites of the present invention include (i) sugar chain-immobilized magnetic metal nano-particles each having a structure in which a sugar chain-immobilized metal nano-particle is bound to a first magnetic nano-particle and (ii) second magnetic particles whose mean particle size is larger than that of the sugar chain-immobilized magnetic metal nano-particles, each of the sugar chain-immobilized metal nano-particles having a structure in which a ligand-conjugate is bound to a metal nano-particle via sulfur atoms, the ligand-conjugate having a structure in which an amino group of a linker compound is connected to a sugar chain having a reducing terminal, and the linker compound including, in molecules thereof, an amino group, a sulfur atom, and a hydrocarbon chain having a carbon-nitrogen bond.

The magnetic composite contains second magnetic particles whose mean particle size is larger than that of the sugar chain-immobilized magnetic metal nano-particles, and therefore the magnetic composite can be more easily collected by a magnetic force than the case of using only the sugar chain-immobilized magnetic metal nano-particles. Accordingly, by binding viruses with sugar chains contained in the magnetic composite and thereafter applying a magnetic force, it is possible to concentrate viruses in a sufficient way almost equal to that in the case of using centrifugation. Therefore, the magnetic composite is preferably used for safely and effectively concentrating target viruses.

In another embodiment, a method for concentrating cells or bacteria includes the step of applying a magnetic force to a mixture containing (i) protein-sugar chain-immobilized magnetic metal nano-particles each having a structure in which a protein is immobilized onto a sugar chain-immobilized magnetic metal nano-particle, (ii) second magnetic particles whose mean particle size is larger than that of the protein-sugar chain-immobilized magnetic metal nano-particles, and (iii) a specimen, the sugar chain-immobilized magnetic metal nano-particle having a structure in which a sugar chain-immobilized metal nano-particle is bound to a first magnetic nano-particle, the sugar chain-immobilized metal nano-particle having a structure in which a ligand-conjugate is bound to a metal nano-particle via sulfur atoms, the ligand-conjugate having a structure in which an amino group of a linker compound is connected to a sugar chain having a reducing terminal, and the linker compound including, in molecules thereof, an amino group, a sulfur atom, and a hydrocarbon chain having a carbon-nitrogen bond.

With the above arrangement, the protein-sugar chain-immobilized magnetic metal nano-particles each have a structure in which a protein is immobilized onto a sugar chain-immobilized magnetic metal nano-particle, and therefore it is possible to cause the protein to specifically bind to the antigen proteins etc. on the surface of cells or bacteria. Further, second magnetic particles whose mean particle size is larger than that of the protein-sugar chain-immobilized magnetic metal nano-particles are used, and therefore it is possible to concentrate cells or bacteria in a sufficient amount almost equal to that of centrifugation concentration. This allows safe and efficient concentration of target cells or bacteria, allowing swift, easy, and highly sensitive detection or identification of cells or bacteria.

Another embodiment of a method for concentrating viruses includes the step of applying a magnetic force to a mixture containing (i) sugar chain-immobilized magnetic metal nano-particles each having a structure in which a sugar chain-immobilized metal nano-particle is bound to a first magnetic nano-particle, (ii) second magnetic particles whose mean particle size is larger than that of the sugar chain-immobilized magnetic metal nano-particles, and (iii) a specimen, each of the sugar chain-immobilized metal nano-particles having a structure in which a ligand-conjugate is bound to a metal nano-particle via sulfur atoms, the ligand-conjugate having a structure in which an amino group of a linker compound is connected to a sugar chain having a reducing terminal, and the linker compound including, in molecules thereof, an aromatic amino group, a sulfur atom, and a hydrocarbon chain having a carbon-nitrogen bond.

Accordingly, the present invention yields an effect of prompt, easy, and highly sensitive detection and identification of viruses.

For a fuller understanding of the properties and advantages of the present invention, reference should be made to the ensuing detailed description taken in conjunction with the accompanying drawings.

BRIEF DESCRIPTION OF THE DRAWINGS

FIG. 1 is a flow chart showing the processes from preparation of the solution 2 to preparation of supernatant supplied to a real time RT-PCR in later-mentioned Example 1.

DESCRIPTION OF THE EMBODIMENTS

Figure 2:
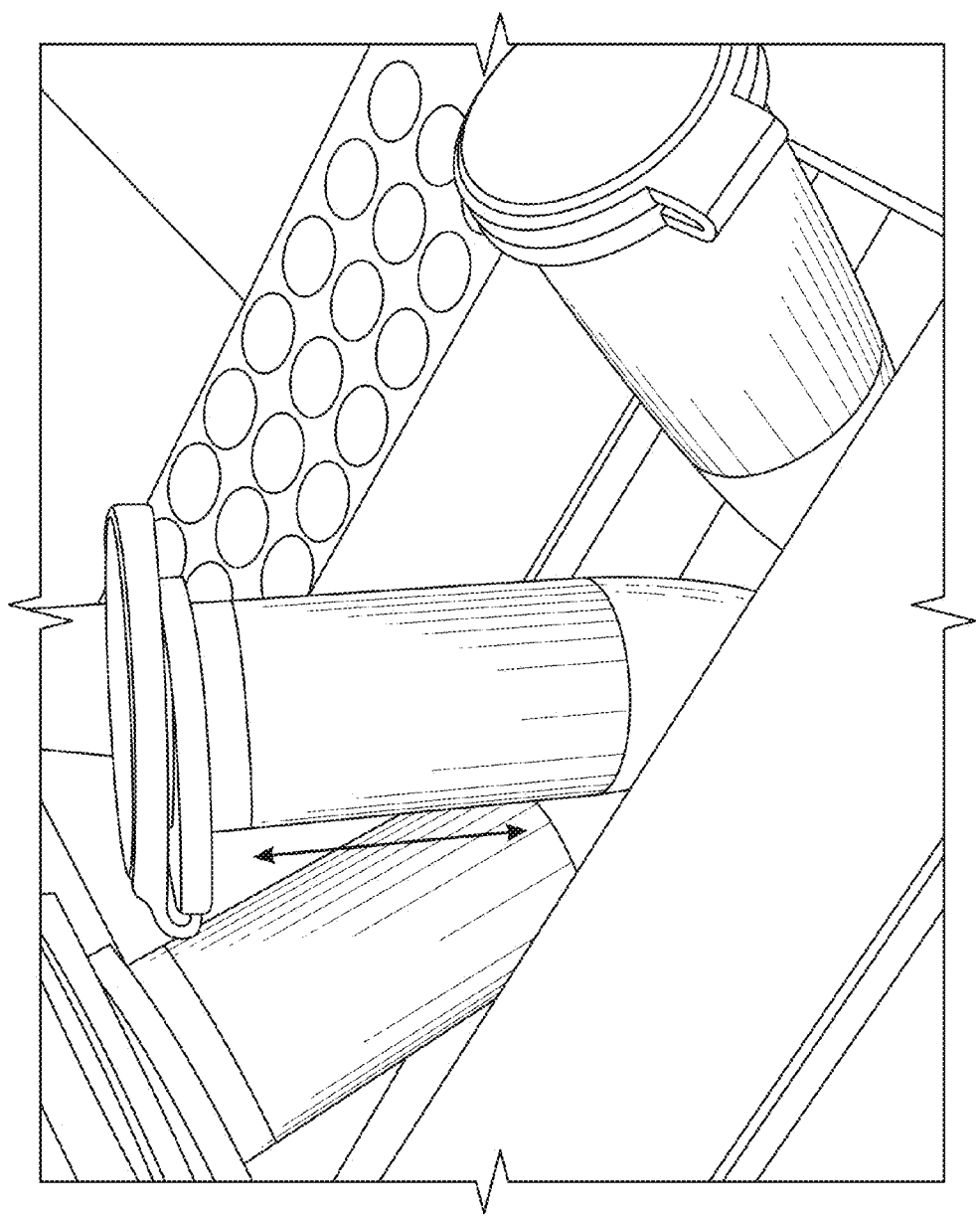
FIG. 2 is a drawing showing application of a magnetic force to a mixture containing sugar chain-immobilized magnetic gold nano-particles in which heparin is immobilized, second magnetic particles, and influenza virus.

The following details the present invention. All of non-patent documents and patent documents mentioned in the specification are incorporated by reference. The following description sets forth numerous exemplary configurations, parameters, and the like. It should be recognized, however, that such description is not intended as a limitation on the scope of the present invention, but is instead provided as a description of exemplary embodiments.

The following details the present invention. In the specification, a wording "A-B" that means a range indicates being not less than A and not more than B.

(1. Method for Concentrating Viruses)

A method of the present invention for concentrating viruses includes the step of applying a magnetic force to a mixture containing (i) sugar chain-immobilized magnetic metal nano-particles each having a structure in which a sugar chain-immobilized metal nano-particle is bound to a first magnetic nano-particle, (ii) second magnetic particles whose mean particle size is larger than that of the sugar chain-immobilized magnetic metal nano-particles, and (iii) a specimen, each of the sugar chain-immobilized metal nano-particles having a structure in which a ligand-conjugate is bound to a metal nano-particle via sulfur atoms, the ligand-conjugate having a structure in which an amino group of a linker compound is connected to a sugar chain having a reducing terminal, and the linker compound including, in molecules thereof, an aromatic amino group, a sulfur atom, and a hydrocarbon chain having a carbon-nitrogen bond.

In the specification, a "sugar chain-immobilized metal nano-particle" indicates a particle having a structure in which a ligand-conjugate is bound to a metal nano-particle via sulfur atoms. Further, a particle obtained by binding a sugar chain-immobilized metal nano-particle to a first magnetic nano-particle is referred to as a "sugar chain-immobilized magnetic metal nano-particle", which is abbreviated as SMGNP.

In the specification, a "ligand-conjugate" is a compound including the linker compound capable of binding to any metal and a sugar chain capable of specifically interacting with protein etc. in a virus, and is a compound having a structure in which a sugar chain having a reducing terminal is connected to an amino group of the linker compound. Therefore, the ligand-conjugate is required to have non-specific interaction based on unspecific hydrophobicity with a substance such as protein.

The linker compound included in the ligand-conjugate has a disulfide group in molecules. This disulfide group produces two sulfur atoms allowing formation of metal-sulfur binding between the linker compound and a metal (e.g. Au—S binding), thereby allowing firm binding between the linker compound and the metal. Consequently, the sugar chain included in the ligand-conjugate is immobilized onto the metal with the intermediation of the linker compound.

The linker compound includes an aromatic amino group and carbon-nitrogen bonds in the molecule. A sugar chain having a reducing terminal is connected to the amino group of the linker compound and the sulfur atom is bound to a metal nano-particle, and therefore it is possible to collectively align sugar chain molecules on the surface of a metal nano-particle. Further, the sugar chain can be easily introduced into the amino group through an optimized reductive amination reaction between a sugar chain having a reducing terminal and an aromatic amino group.

The metal nano-particle indicates a colloidal metal particle whose mean particle size is preferably not less than 1 nm and less than 100 nm. When the mean particle size is less than 1 nm, it is difficult to prepare nano-particles. When the mean particle size is not less than 100 nm, colloid itself may precipitate, resulting in a possibility that the binding reaction with viruses does not occur promptly. Further, since the size of a virus is approximately 100 nm, use of a particle whose size is larger than that of a virus may decrease the efficiency in binding to the virus. How to calculate mean particle size will be mentioned later.

The metal includes gold, silver, copper, aluminum, platinum, aluminum oxide, $SrTiO_3$, $LaAlO_3$, $NdGaO_3$, $ZrO_2$, etc. Gold is particularly preferable. In a case of gold, chloroauric acid or salts thereof are preferable, and chloroauric acid is more preferable, in view of availability. How to obtain the metal nano-particle is not particularly limited. For example, the metal nano-particle can be obtained in such a manner that a metal acid or salts thereof is dissolved in methanol, water, a mixture solvent thereof or the like and is reduced with citric acid etc. to change metal ions (e.g. gold ions) to a metal (e.g. gold). A specific example of the metal acid or salts thereof is hydrogen (III) chloride (Aurochloric acid) or sodium gold (III) chloride (Aurochloric acid sodium salt).

In the ligand-conjugate, a sugar chain having a reducing terminal is connected to an aromatic amino group of the linker compound. In other words, the ligand-conjugate has a structure in which the linker compound is connected to the sugar chain having a reducing terminal via an amino group. Introduction of the sugar chain can be carried out by a reductive amination reaction between the amino group (—$NH_2$ group) of the linker compound and a reducing terminal of sugar chain. That is, an aldehyde group (—CHO group) or a ketone group (—CRO group, R is a hydrocarbon group) of the reducing terminal of sugar chain in an equilibrium state reacts with the amino group included in the linker compound to produce Schiff base. By the subsequent reduction of the Schiff base generated by the reaction, it is possible to easily introduce a sugar chain to an amino group in a stable form.

When preparing the ligand-conjugate, it is preferable to mix the linker compound with the sugar chain at a molar ratio of 1:1 to 50:1.

The "sugar chain having a reducing terminal" is a monosaccharide chain, an oligosaccharide chain, or a polysaccharide in which the anomeric carbon atoms at their reducing terminal are not replaced. That is, the "sugar chain having a reducing terminal" is a reducing sugar chain. Examples of the sugar chain having a reducing terminal include commercially available ones, natural ones, synthesized ones, and ones prepared by the specific decomposition of commercially available polysaccharide or natural polysaccharide chains.

More specific examples of the sugar chain having a reducing terminal include glucose, galactose, mannose, maltose, isomaltose, lactose, panose, cellobiose, mellibiose, mannooligosaccharide, chitooligosaccharide, laminari-oligosaccharide, glucosamine, N-acetylglucosamine, glucuronic acid, heparine, heparan sulfate, chondroitin, chondroitin sulfate, and dermatan sulfate. However, the sugar chain is not limited to these, and a sugar chain that is recognized by viruses to be concentrated is selected appropriately and is connected to the linker compound.

The linker compound is not particularly limited as long as it contains, in its molecules, one or more amino groups, a sulfur atom, and a hydrocarbon chain having carbon-nitrogen bonds. Accordingly, a conventional and publicly known linker compound, such as a linker compound having been developed by the inventors of the present invention, may be used preferably.

carbon atoms and/or hydrogen atoms may be replaced with other atom or substituent. For example, the hydrocarbon chain may be a hydrocarbon chain in which at least one carbon-carbon bond (C—C bond) is replaced with a carbon-nitrogen bond (C—N bond), or may be a hydrocarbon chain in which a part of carbon-carbon bonds is replaced with a carbon-nitrogen bond, carbon-oxygen bond (C—O bond), an amide bond (CO—NH bond) etc. The amino group is used to connect the linker compound with a sugar chain, and the sulfur atom is used to immobilize the ligand-conjugate onto a metal.

It is preferable that the amino group is positioned at an end of the hydrocarbon chain in order to facilitate connecting with a sugar chain. The amino group may be a modified amino group. Examples of the modified amino group include an amino group modified with an acetyl group, a methyl group, a formyl group etc. and an aromatic amino group. Of course, the amino group may be an unmodified amino group. The aromatic amino group is particularly preferable. It is necessary that an amino group is not protonated under pH3-4, which is a condition most suitable for a reductive amination reaction. Accordingly, the amino group is preferably an aromatic amino group in which conjugation with an aromatic series allows an unshared electron pair to exist on nitrogen atoms under pH3-4.

The sulfur atom exists in such a manner that a part of the carbons in the hydrocarbon chain is replaced with sulfur, and is capable of easily forming a metal-sulfur bond. Accordingly, it is preferable that the sulfur atom is included, as disulfide group (S—S group) or a thiol group (SH group), in the hydrocarbon chain. In the hydrocarbon chain, a hydrocarbon structure including one or more sulfur atoms may be a ring structure with a five-membered ring that includes disulfide group as in cases of compounds represented by later-mentioned general formulae (1) to (4) and (6), or may be a chain structure, such as a compound represented by general formula (5). Further, the chain structure may be a branched or non-branched chain structure.

The linker compound may be one of the following linker compounds described in WO2005/077965 or U.S. Pat. No. 7,320,867 for example.

The linker compound may be one of the following compounds. A compound having a structure represented by general formula (1)

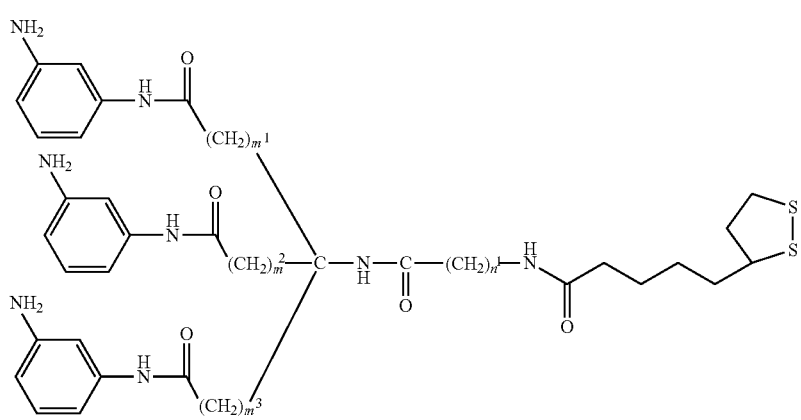

(1)

The hydrocarbon chain should be such that a main chain contains at least one carbon-nitrogen bond. Further, a part of wherein $m^1$, $m^2$, and $m^3$ independently indicate an integer of 0 to 6, and $n^1$ indicates an integer of 1 to 6.

A compound having a structure represented by general formula (2)

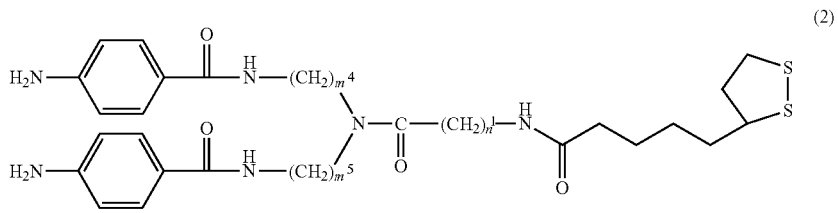

(2)

wherein $m^4$ and $m^5$ independently indicate an integer of 0 to 6, and $n^1$ indicates an integer of 1 to 6.

A compound having a structure represented by general formula (3)

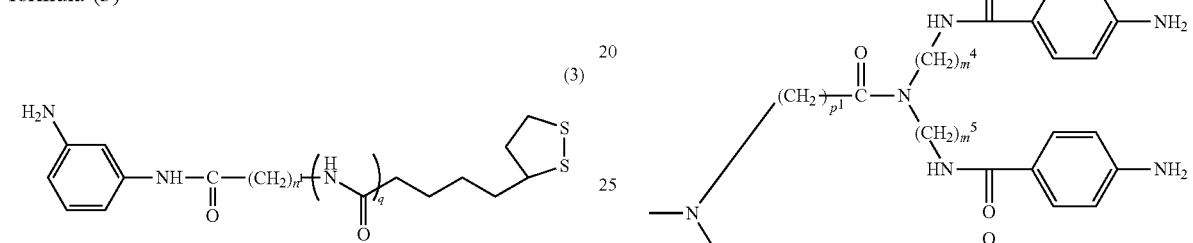

(3)

wherein $n^1$ and $q$ independently indicate an integer of 0 to 6.

A compound having a structure represented by general formula (4)

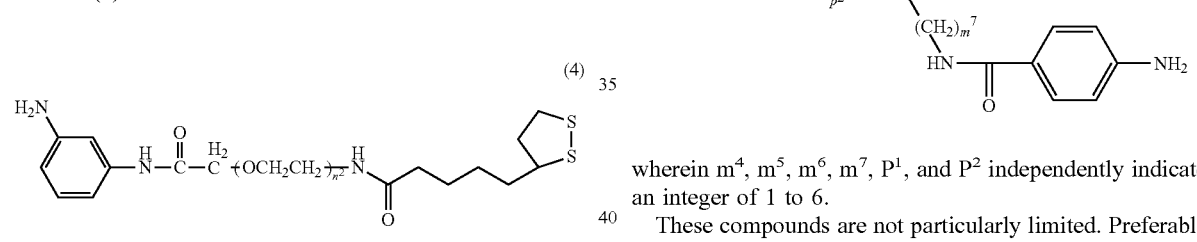

(4)

wherein $n^2$ is an integer of 1 to 6.

A compound having a structure represented by general formula (5)

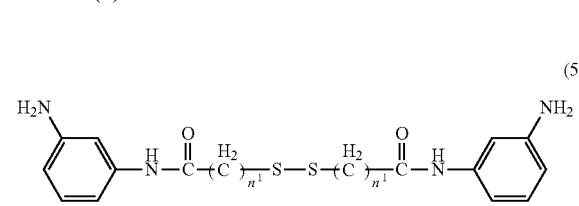

(5)

wherein $n^1$ is an integer of 1 to 6.

A compound having a structure represented by general formula (6)

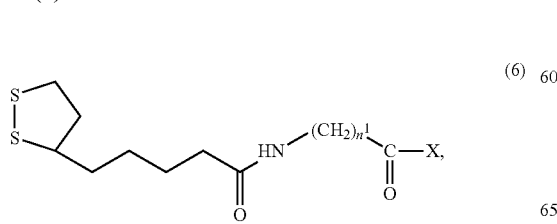

(6)

wherein $n^1$ is an integer of 1 to 6, and X is represented by general formula (7)

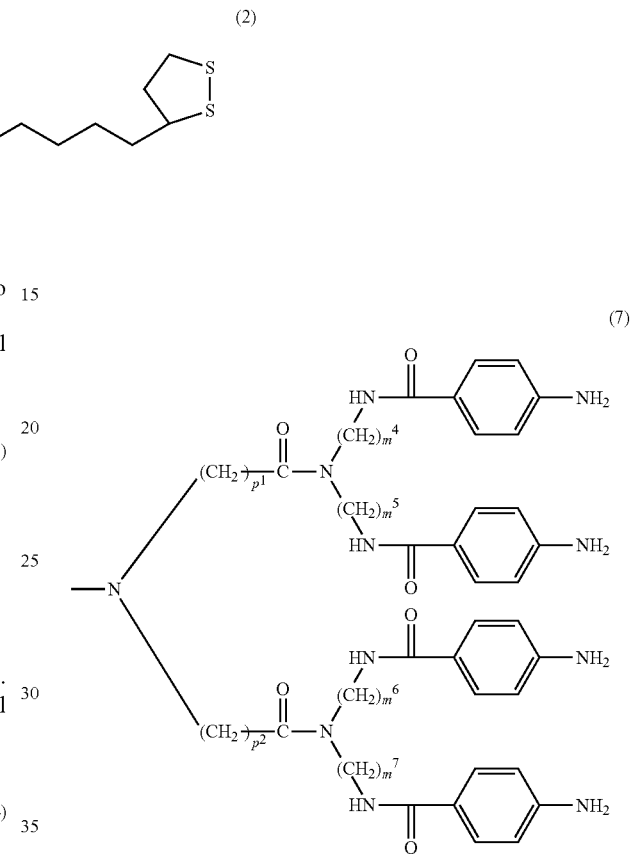

(7)

wherein $m^4$, $m^5$, $m^6$, $m^7$, $P^1$, and $P^2$ independently indicate an integer of 1 to 6.

These compounds are not particularly limited. Preferable examples of the compounds include a compound represented by general formula (1) wherein $m^1$, $m^2$, and $m^3$ indicates 1 and $n^1$ indicates 1, a compound represented by general formula (2) wherein $m^4$ and $m^5$ indicate 2 and $n^1$ indicates 1, a compound represented by general formula (3) wherein $n^1$ and $q$ indicate 0, a compound represented by general formula (4) wherein $n^2$ is 4, and a compound represented by general formula (5) wherein $n^1$ is 3.

The linker compound may be a compound having a structure represented by general formula (8), which is described in J. Biochem., 146(1), 33-41 (2009) for example.

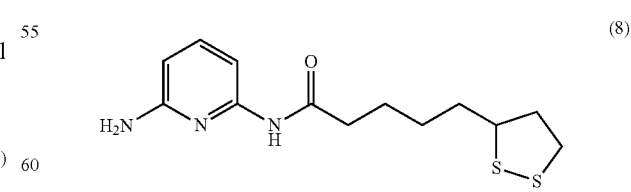

(8)

The linker compound can be produced by conventional and publicly known methods disclosed, for example, in WO 2005/077965 publication, U.S. Pat. No. 7,320,867, etc. For example, the linker compounds represented by the general formulae (1), (2), (3), (6) and (8) can be produced by concentration-reacting thioctic acid with an amine compound whose aromatic amino group terminal is protected by a protective group, and deprotecting the protective group at the aromatic amino group terminal. Further, the linker compound represented by the general formula (5) can be produced by concentration-reacting a dimmer of γ-mercapto butyric acid with an amine compound whose aromatic amino group terminal of two molecules is protected by a protective group and deprotecting the protective group at the aromatic amino group terminal.

Since the sugar chain-immobilized metal nano-particles can be manufactured only by mixing the ligand-conjugate and a solution containing the metal, it is possible to very easily immobilize sugar chains.

In the method of the present invention for concentrating viruses, sugar chain-immobilized magnetic metal nano-particles obtained by binding sugar chain-immobilized metal nano-particles with first magnetic nano-particles are used. In the specification, the "first magnetic nano-particle" indicates a magnetic nano-particle to which a metal included in a sugar chain-immobilized metal nano-particle is bound.

The magnetic nano-particle is not particularly limited, and may be a conventional and publicly known magnetic nano-particle. Examples of the magnetic nano-particle include iron oxide, magnetite, chromium oxide, cobalt, ferrite, nickel, and gadolinium. In particular, it is preferable that the first magnetic nano-particle and the second magnetic particle are independently selected from iron oxide, magnetite, or ferrite, since these metals allow depositing, on their surfaces, the metal of the sugar chain-immobilized metal nano-particles. In the specification, iron oxide indicates iron (III) oxide. Magnetite indicates iron (II) and iron (III) oxide ($Fe^{2+}Fe^{3+}_2O_4$). The first magnetic nano-particle and the second magnetic particle may be different, but it is preferable that the first magnetic nano-particle and the second magnetic particle possess the same composites. For example, it is preferable that both of the particles are magnetite.

"A structure in which a sugar chain-immobilized metal nano-particle is bound to a first magnetic nano-particle" indicates a structure in which a metal included in the metal nano-particle is bound to the first magnetic nano-particle. The manner of the binding is not particularly limited. For example, the manner of the binding may be such that the metal is deposited on the surface of the first magnetic nano-particle through metallic bond or nonspecific adsorption.

As described above, in the specification, a particle having a structure in which a sugar chain-immobilized metal nano-particle is bound to the first magnetic nano-particle is referred to as a "sugar chain-immobilized magnetic metal nano-particle". How to prepare the sugar chain-immobilized magnetic metal nano-particle is not particularly limited. For example, the sugar chain-immobilized magnetic metal nano-particle may be prepared in such a manner that a metal ion to be bound to a sulfur atom in a ligand-conjugate is mixed with the first magnetic nano-particle in a solvent to deposit the metal on the surface of the first magnetic nano-particle, and thereafter mixed with the ligand-conjugate and the resultant is subjected to a reducing process. Consequently, a sulfur atom included in the ligand-conjugate in the form of S—S bond etc. is immobilized to the metal through metal-sulfur bind such as Au—S bind, so that a sugar chain-immobilized magnetic metal nano-particle can be prepared.

The solvent is not particularly limited. Examples of the solvent include water, methanol, and a mixed solvent of water and methanol. Further, a reducing agent used in the reducing process is not particularly limited. Examples of the reducing agent include sodium borohydride, citric acid and salt thereof, ascorbic acid and salt thereof, phosphorous, tannic acid and salt thereof, ethanol, and hydrazine.

In a solution in which the metal ion, the first magnetic nano-particle, the ligand-conjugate, and the reducing agent are mixed, when the metal is chloroauric acid or salt thereof, final concentration of chloroauric acid or salt thereof in the solution preferably ranges from 0.5 mM to 30 mM, and more preferably ranges from 1 mM to 10 mM. Final concentration of the reducing agent in the solution is preferably a molar concentration that is three to twenty times larger than a molar concentration of a gold ion, and is more preferably a molar concentration that is five to ten times larger than a molar concentration of a gold ion. Final concentration of the ligand-conjugate in the solution preferably ranges from 0.1 mM to 100 mM, and more preferably ranges from 1 mM to 10 mM. Final Fe concentration of the first magnetic nano-particle in the solution preferably ranges from 0.5 mM to 10 mM, and more preferably ranges from 1 mM to 5 mM.

The ligand-conjugate avoids the non-specific interaction with protein based on the non-specific hydrophobic interaction. Accordingly, use of the ligand-conjugate allows reproducible evaluation of interaction between the sugar chain and proteins of viruses.

The resulting sugar chain-immobilized metal nano-particle in the solution can be put in a more stable state by applying a magnetic force thereto and removing non-magnetic components such as low molecular salt.

The range of mean particle size of the sugar chain-immobilized magnetic metal nano-particle is not particularly limited as long as the mean particle size is in the nano scale (not less than 1 nm and less than 1 μm) and is smaller than mean particle size of the second magnetic particle mentioned later. However, the mean particle size is preferably not less than 1 nm and less than 100 nm, and is more preferably not less than 2 nm and not more than 50 nm.

The mean particle size of the first magnetic nano-particle is not particularly limited as long as the mean particle size of the first magnetic nano-particle allows the mean particle size of the sugar chain-immobilized magnetic metal nano-particle to be in the nano scale (more than 1 nm and less than 1 μm) and be smaller than the mean particle size of the second magnetic particle. However, the mean particle size of the first magnetic nano-particle is preferably a size that allows the mean particle size of the sugar chain-immobilized magnetic metal nano-particle to be not less than 1 nm and less than 100 nm, and more preferably a size that allows the mean particle size of the sugar chain-immobilized magnetic metal nano-particle to be not less than 2 nm and not more than 50 nm.

Further, the range of the mean particle size of the second magnetic particle is not particularly limited as long as the mean particle size of the second magnetic particle is not more than 100 μm and is larger than the mean particle size of the sugar chain-immobilized magnetic metal nano-particle. However, the mean particle size of the second magnetic particle is preferably not less than 100 nm and not more than 100 μm, and more preferably not less than 100 nm and not more than 50000 nm, and further preferably not less than 1000 nm and not more than 10000 nm.

The inventors of the present invention confirmed that in a case where the second magnetic particle was not used and only the sugar chain-immobilized magnetic metal nano-particle was used, only applying a magnetic force did not yield the same concentration efficiency as in a case of centrifugation (see control in later-mentioned Example 1).

Subsequently, the inventors of the present invention discussed whether enlarging the particle size of the sugar chain-immobilized magnetic metal nano-particle would solve this problem or not, and found that enlarging the particle size of the sugar chain-immobilized magnetic metal nano-particle did not yield the same concentration efficiency as in a case of centrifugation, either (see Comparative Example 1 mentioned later).

The inventors of the present invention have diligently studied and found that use of not only the sugar chain-immobilized magnetic metal nano-particle but also a second magnetic particle whose mean particle size is greater than that of the sugar chain-immobilized magnetic metal nano-particle allows concentration efficiency substantially equal to that in the case of centrifugation.

It is supposed that setting the mean particle size of the sugar chain-immobilized magnetic metal nano-particle and the mean particle size of the second magnetic particle to be in the above ranges, respectively, optimizes the mean particle sizes thereof. By applying a magnetic force to a mixture including the sugar chain-immobilized magnetic nano-particle, the second magnetic particle, and a specimen, when viruses are contained in the specimen, it is possible to concentrate a small amount of viruses in the specimen more efficiently, more easily, and more safely, without using centrifugation.

The sugar chain-immobilized magnetic metal nano-particle tends to be bound to virus. However, the sugar chain-immobilized magnetic metal nano-particle has a low magnetic force due to the small size. Consequently, it is supposed that when only the sugar chain-immobilized magnetic metal nano-particle is used, effective concentration of viruses by a magnetic force from an outside magnetic field is difficult due to the Brownian movement. In contrast thereto, when not only the sugar chain-immobilized magnetic metal nano-particle but also the second magnetic particle are used, the mixture containing the sugar chain-immobilized magnetic metal nano-particle, the second magnetic particle, and a specimen has a magnetic force large enough to overcome the Brownian movement. Consequently, it is supposed that application of a magnetic force from an outside magnetic field allows effective concentration of viruses.

In the specification, "particle size" indicates the diameter of the maximum inscribed circle of a two-dimensional shape of a particle seen by a transmission electron microscope. For example, if the two-dimensional shape of a particle is substantially circular, the "particle size" indicates the diameter of the circle. If substantially elliptic, the "particle size" indicates the minor axis of the ellipse. If substantially square, the "particle size" indicates a side of the square. If substantially rectangular, the "particle size" indicates a short side of the rectangle. The "mean particle size" indicates a mean value of particle sizes of a plurality of particles. In the specification, whether the mean particle size is in a predetermined range or not was determined by observing 20 particles by a transmission electron microscope, measuring particle sizes of individual particles, and calculating the mean value of the particle sizes of the 20 particles.

According to the method of the present invention, a magnetic force is applied to a mixture containing the sugar chain-immobilized magnetic metal nano-particle, the second magnetic particle whose mean particle size is larger than that of the sugar chain-immobilized magnetic metal nano-particle, and a specimen. When the specimen contains virus, the virus is bound to a sugar chain of the sugar chain-immobilized magnetic metal nano-particle. The specimen is not particularly limited as long as it is capable of contacting the sugar chain-immobilized magnetic metal nano-particle. Examples of the specimen include saliva, nasal mucosa, body fluids of plants and animals etc. They may be used directly as specimens, or may be used in the form of a liquid prepared by adding them to a MEM culture medium, physiological saline etc. By mixing such specimen with a solution prepared by adding the sugar chain-immobilized magnetic metal nano-particle to water, physiological saline, or phosphate buffer etc., it is possible to make viruses in the specimen contact with the sugar chain-immobilized magnetic metal nano-particles.

Viruses inherently recognize sugar chains. Therefore, by preparing sugar chain-immobilized magnetic metal nano-particles using sugar chains that can be recognized by viruses to be concentrated and by making the specimen contact with the sugar chain-immobilized magnetic metal nano-particles, if the specimen contains viruses, the viruses specifically bind to the sugar chains.

Viruses to be concentrated are not particularly limited. Examples of such viruses include influenza virus, simple herpes virus, venereal herpes virus, AIDS virus, Hepatitis B virus, Hepatitis C virus, varicella virus (VZV), cytomegalovirus (CMV), adult T-cell leukemia virus (HTLV-1), lentivirus, koi herpesvirus, adenovirus, Norovirus, rotavirus, enterovirus, and bovine viral diarrhea virus (BVDV).

Examples of sugar chains that can be specifically recognized by influenza virus include heparin, NeuAcα2-6Galβ1-4GlcNAcβGlc, NeuAcα2-6Galβ1-3GlcNAcβGlc, NeuAcα2-3Galβ1-4GlcNAcβGlc, and NeuAcα2-3Galβ1-3GlcNAcβGlc.

By selecting one of these sugar chains, preparing sugar chain-immobilized magnetic metal nano-particles, and making the sugar chain-immobilized magnetic metal nano-particles contact with a specimen, if the specimen contains viruses, the viruses are specifically bound to the sugar chain.

Examples of the sugar chains that can be specifically recognized by simple herpes virus, venereal virus, varicella virus (VZV), cytomegalovirus (CMV), lentivirus, koi herpesvirus, adenovirus, and enterovirus include: heparin, heparan sulfate, disaccharide structures that constitute heparan sulfate, chondroitin sulfate, and disaccharide structures that constitute chondroitin sulfate.

Examples of the sugar chains that can be specifically recognized by AIDS virus (HIV) and adult T-cell leukemia virus (HTLV-1) include heparin, heparan sulfate, disaccharide structures that constitute heparan sulfate, and dermatan sulfate. Examples of the sugar chains that can be specifically recognized by Noro virus include fucose and N-acetylgalactosamine. An example of the sugar chain that can be specifically recognized by rotavirus is lactose. Examples of sugar chains that can be specifically recognized by Hepatitis C virus and bovine viral diarrhea virus include N-acetylglucosamine, heparin, and heparan sulfate.

When the influenza virus exists in a specimen approximately in the hemagglutinin unit of $1\times10^{-6}$ (HAU), the method of the present invention allows concentrating the viruses selectively, easily and safely in a short time without using centrifugation. Accordingly, subjecting the specimen to real time PCR for example allows sufficiently detecting the viruses in the specimen.

It is preferable that the weight ratio of the sugar chain-immobilized magnetic metal nano-particle to the second magnetic particle is in a range of $1:1\times10^3$ to $1:1\times10^{11}$. When the ratio in the consumed amount of the sugar chain-immobilized magnetic metal nano-particle to the second magnetic particle, mean particle sizes of both particles being in the above relation, is set to be in the above range, it is possible to further increase concentration efficiency.

As for "apply a magnetic force", how to apply a magnetic force is not particularly limited. For example, by attaching a conventional and publicly known permanent magnet such as an electromagnet and bar magnet to an external wall of a vessel containing the mixture, it is possible to apply a magnetic force to the mixture. In order to realize concentration efficiency almost equal to that in the case of centrifugation, the intensity of a magnetic force is preferably in a range of 100 to 500 millitesla.

When a step of applying a magnetic force to the mixture is to be ended may be determined based on such a phenomenon that coloring due to dispersion of the sugar chain-immobilized magnetic metal nano-particle to a liquid is thinned by adsorption of the sugar chain-immobilized magnetic metal nano-particle onto the second magnetic particle.

By applying a magnetic force, the sugar chain-immobilized magnetic metal nano-particles which bind to viruses and the second magnetic particles are accumulated. Collecting virus genes from the accumulate is not particularly limited and may be performed through a conventional and publicly known method. For example, by washing the accumulate with sterilized water or distilled water, pipetting appropriately, and heating the resulting suspension with the sterilized water or distilled water containing the accumulate at 100° C., it is possible to collect virus genes in the supernatant.

It is preferable that the mixture is obtained by mixing (i) specimen-contacted magnetic metal nano-particles obtained by contacting sugar chains of the sugar chain-immobilized magnetic metal nano-particles with a specimen with (ii) the second magnetic particles. Consequently, when the specimen contains viruses, the viruses recognize the sugar chains and are bound to the sugar chains and thereafter the second magnetic particles are mixed. This realizes prompter binding of the viruses and the sugar chains. Contacting of the sugar chain-immobilized magnetic metal nano-particles with viruses in the specimen may be performed by mixing (i) a solution prepared by adding the sugar chain-immobilized magnetic metal nano-particles to water, physiological saline, or phosphate buffer with (ii) the specimen. After the mixing, by stirring the mixture by a method such as pipetting for example, it is possible to bind viruses with sugar chains more surely. This reduces a time necessary for binding of viruses with sugar chains.

To "recognize" as mentioned above indicates binding of surface protein of a virus with a sugar chain via a sugar-binding site (sugar chain recognition site) in molecules of the surface protein. Examples of the binding include hydrogen binding, ion binding, binding by electrostatic interaction, and binding by van der Waals force.

A method for confirming the result of concentration of viruses through the method of the present invention is not particularly limited, and a conventional and publicly known method may be used. Examples of the method for confirming collected viruses include PCR, real time PCR, northern blotting, immunochromatography, and ELISA. In particular, real time PCR is preferable since it allows prompt determination of the quantity of genes. In a case of real time PCR, a difference is calculated by subtracting a Ct (Threshold Cycle) value after concentration from a Ct value before concentration. If the difference calculated when concentration is made through the method of the present invention is almost equal to that calculated when concentration is made through centrifugation, an object of the present invention may be considered to be solved.

(2. Magnetic Composite and Concentrating Device)

A magnetic composite of the present invention includes (i) sugar chain-immobilized magnetic metal nano-particles each having a structure in which a sugar chain-immobilized metal nano-particle is bound to a first magnetic nano-particle and (ii) second magnetic particles whose mean particle size is larger than that of the sugar chain-immobilized magnetic metal nano-particles, each of the sugar chain-immobilized metal nano-particles having a structure in which a ligand-conjugate is immobilized onto a metal nano-particle via sulfur atoms, the ligand-conjugate having a structure in which an amino group of a linker compound is connected to a sugar chain having a reducing terminal, and the linker compound including, in molecules thereof, an amino group, a sulfur atom, and a hydrocarbon chain having carbon-nitrogen bonds.

The "sugar chain-immobilized metal nano-particle", the "first magnetic nano-particle", the "sugar chain-immobilized magnetic metal nano-particle", and the "second magnetic particle" have been already explained above. The magnetic composite is mixed with a specimen. Accordingly, when the specimen contains viruses, the viruses are bound to a sugar chain of the sugar chain-immobilized magnetic metal nano-particles. Since the magnetic composite contains the second magnetic particles, applying a magnetic force to the magnetic composite after binding the viruses with the sugar chains of the sugar chain-immobilized magnetic metal nano-particles allows concentration of the viruses.

The magnetic composite may be prepared by mixing a solution of the sugar chain-immobilized magnetic metal nano-particles prepared as above with the second magnetic particles. In this preparation, it is preferable that the mixing is made so that the weight ratio of the sugar chain-immobilized magnetic metal nano-particles to the second magnetic particles is in a range of $1:1\times10^3$ to $1:1\times10^{11}$.

A concentrating device of the present invention includes at least the magnetic composite of the present invention and a magnet. The concentrating device may further include: storage sections for storing a specimen, the magnetic composite, buffer etc., respectively; a pump for sucking the specimen, the magnetic composite, the buffer etc. from the storage sections; an electromagnetic valve for adjusting the amount to be sucked; a chamber for mixing the specimen, the magnetic composite, buffer etc.

For example, after mixing the specimen with the magnetic composite, a magnetic force is applied to the resulting mixture by a magnet. This allows precipitating the magnetic composite to which viruses are bound. A method for collecting the viruses from the precipitate has been already explained above. The concentrating device may be used not only as a concentrating device for concentrating viruses but also as a concentrating device for concentrating bacteria etc. capable of recognizing a sugar chain.

(3. Measurement Method of Protein-Sugar Chain Interaction)

A solution containing a sugar chain-immobilized magnetic metal nano-particle including a structure in which the sugar chain-immobilized metal nano-particle is bound to a first magnetic nano-particle is mixed with protein capable of recognizing sugar chain positioned at an end of the sugar chain-immobilized magnetic metal nano-particle so that the sugar chain and the protein interact to each other and protein-sugar chain interacting particle precipitates are produced. This allows measuring protein-sugar chain interaction. Hereinafter, a method for measuring the protein-sugar chain interaction is referred to as a "measurement method of protein-sugar chain interaction".

The "solution containing a sugar chain-immobilized magnetic metal nano-particle" indicates a liquid in which the sugar chain-immobilized magnetic metal nano-particles are dispersed. The solution may contain salt etc. in addition to the sugar chain-immobilized magnetic metal nano-particles. The liquid may be water, or buffer etc.

The protein is not particularly limited as long as it is capable of recognizing a sugar chain positioned at an end of the sugar chain-immobilized magnetic metal nano-particle. For example, in a case where the sugar chain positioned at an end of the sugar chain-immobilized magnetic metal nano-particle is glucose, the protein may be one capable of recognizing glucose, such as concanavalin A (ConA), lentil lectin (LCA), and peanut lectin (PSA).

Similarly, in a case where the sugar chain positioned at an end of the sugar chain-immobilized magnetic metal nano-particle is galactose, the protein may be one capable of recognizing galactose, such as *Ricinus communis* agglutinin lectin (RCA120). Further, in a case where the sugar chain positioned at an end of the sugar chain-immobilized magnetic metal nano-particle is N-acetylglucosamine, the protein may be one capable of recognizing N-acetylglucosamine, such as wheat germ lectin (WGA).

A method for mixing the solution containing the sugar chain-immobilized magnetic metal nano-particle with protein capable of recognizing a sugar chain positioned at an end of the sugar chain-immobilized magnetic metal nano-particle is not particularly limited as long as the method allows interaction between the sugar chain and the protein. For example, the mixing may be carried out in such a manner that a dilution series of protein is prepared in a microplate, Eppendorf tube etc., and the solution containing the sugar chain-immobilized magnetic metal nano-particle is added to the dilution series and the resultant is left.

Examples of the interaction between a sugar chain and protein (hereinafter "protein-sugar chain interaction") include a hydrogen bond, an ionic bond, an electrostatic interaction, and van der Waals force. That is, the protein recognizes the sugar chain positioned at an end of the sugar chain-immobilized magnetic metal nano-particle, and consequently a protein-sugar chain interaction such as hydrogen bond occurs.

The "protein-sugar chain interacting particle precipitate" indicates agglomerate generated as a result of interaction and specific binding between a sugar chain and protein. The protein-sugar chain interaction can be visually observed as production of a protein-sugar chain interacting particle precipitate. When a sugar chain and protein do not interact to each other, the protein-sugar chain interacting particle precipitate is not produced.

An example of a method for measuring interaction between substances by confirming agglutination reaction is a latex agglutination method using antigen-antibody reaction ("Development and evaluation of bio-diagnostic products and corporations", CMC technical library 146, CMC publishing, p 92-97, p 109-113). The latex agglutination method is carried out in such a manner that antibodies are immobilized on a surface of the latex, a dilution series of a sample antigen is prepared using a microplate having 96 holes, a maximum dilution rate that causes agglomeration is calculated, and the maximum dilution rate is compared with that of a standard solution so as to measure interaction between substances. The result obtained in the measurement is absorbance of light with respect to light with a certain wavelength.

However, a known method for measuring interaction between substances by confirming agglomeration reaction of colloid is only a method for determining a result based on red color exhibited by relative small particles and purple color exhibited by relatively large particles. Therefore, the "measurement method of protein-sugar chain interaction", which causes a sugar chain and protein in colloid to interact to each other so as to produce agglomerate and confirms production of the agglomerate so as to determine the result, is much easier and useful method compared with a conventional method.

The "measurement method of protein-sugar chain interaction" allows measurement of protein-sugar chain interaction without using a marker. Accordingly, this method is easier in that it does not require a pre-process, compared with a method using a marker. Further, since this method is free from such a problem that a marker effect causes great variations in measurement, this method allows reproducible measurement. Further, in this method, it is possible to visually observe protein-sugar chain interaction. Accordingly, this method does not require any special device, allowing very low-cost and easy measurement of protein-sugar chain interaction.

Therefore, the "measurement method of protein-sugar chain interaction" is applicable to analysis of functions of sugar chain and protein and to inspection and diagnosis.

The "measurement method of protein-sugar chain interaction" should include the step of producing a protein-sugar chain interacting particle precipitate by mixing a solution containing sugar chain-immobilized magnetic metal nano-particles with protein capable of recognizing sugar chain positioned at an end of the sugar chain-immobilized magnetic metal nano-particles and causing the sugar chain and the protein to interact to each other. Production of the protein-sugar chain interacting particle precipitate may be only visually observed as described above, or if more detailed measurement is necessary, the method may further include the step of measuring ultraviolet-visible absorption spectrum with respect to a certain wavelength.

(4. Method for Collecting Protein from Protein-Sugar Chain Interacting Particle Precipitate)

In one embodiment of the present invention, a method for collecting protein from the protein-sugar chain interacting particle precipitate includes the steps of: producing a protein-sugar chain interacting particle precipitate by mixing a solution containing sugar chain-immobilized magnetic metal nano-particles with protein capable of recognizing sugar chain positioned at an end of the sugar chain-immobilized magnetic metal nano-particles and causing the sugar chain and the protein to interact to each other; and mixing the protein-sugar chain interacting particle precipitate with water in such a manner that pH of a mixture solution is not more than 5.

The step of "mixing the protein-sugar chain interacting particle precipitate with water in such a manner that pH of a mixture solution is not more than 5" includes the substeps of separating, using a magnetic force etc., the protein-sugar chain interacting particle precipitate produced as a result of the protein-sugar chain interaction; and mixing the protein-sugar chain interacting particle precipitate with water in such a manner that pH of a mixture solution is not more than 5. Acid for making pH of the mixture solution not more than 5 is not particularly limited, and examples of the acid include hydrochloric acid, sinapic acid, nitric acid, and sulfuric acid.

By setting pH of the mixture solution to be not more than 5, the mixture solution gets acidic. This allows isolating protein from a sugar chain site of the protein-sugar chain interacting particle precipitate. Alternatively, by setting pH of the mixture solution to be not more than 5, a structure of protein constituting the protein-sugar chain interacting particle precipitate gets denatured and the sugar chain loses its ability to recognize protein. This allows completely isolating protein from the protein-sugar chain interacting particle precipitate.

As described in later-mentioned Examples, protein disassociated from the protein-sugar chain interacting particle precipitate can be distinctly disassociated from the sugar chain-immobilized magnetic metal nano-particles, too. This allows easy collection of protein. Further, the disassociated protein may be identified using polyacrylamide gel electrophoresis, quantity determination of protein, mass spectroscopy etc. The mass spectrometry may be carried out through a conventional and publicly known method using a conventional and publicly known mass spectrometer such as a matrix-assisted laser desorption/time-of-flight mass spectrometer (MALDI-TOF/MS).

In one embodiment of the present invention, the method for collecting protein from a protein-sugar chain interacting particle precipitate includes the steps of: producing protein-sugar chain interacting particle precipitate by causing a solution containing sugar chain-immobilized magnetic metal nano-particles and protein capable of recognizing a sugar chain of the sugar chain-immobilized magnetic metal nano-particles to be mixed with each other; separating the protein-sugar chain interacting particle precipitate by using a magnetic force etc.; and mixing the protein-sugar chain interacting particle precipitate with a sugar chain capable of recognizing the protein.

In the step of mixing the protein-sugar chain interacting particle precipitate with a sugar chain capable of recognizing the protein, the protein-sugar chain interacting particle precipitate produced as a result of the interaction between sugar chain and protein is collected using a method such as centrifugation, and sugar chain capable of recognizing protein that constitutes the protein-sugar chain interacting particle precipitate is added to and mixed with the collected protein-sugar chain interacting particle precipitate.

It is supposed that the mixture causes substitution reaction between protein constituting the protein-sugar chain interacting particle precipitate and the sugar chain capable of recognizing the protein, thereby disassociating the protein from the protein-sugar chain interacting particle precipitate.

A method for mixing in the step of "mixing the protein-sugar chain interacting particle precipitate with a sugar chain capable of recognizing the protein" is not particularly limited, and stirring may or may not be carried out. Since this step is a step involving substitution using affinity between the sugar chain constituting the protein-sugar chain interacting particle precipitate and the sugar chain capable of recognizing the protein, it is preferable that the sugar chain capable of recognizing the protein is added in an excessive amount.

The disassociated protein can be identified by using polyacrylamide gel electrophoresis, quantity determination of protein, mass spectroscopy etc.

Further, in a case of reacting protein with the sugar chain-immobilized magnetic metal nano-particles, when various sugar chains which the protein can recognize are added to the sugar chain-immobilized magnetic metal nano-particles, agglomeration due to protein-sugar chain interaction can be prevented. This allows analyzing functions of the protein in more detail. For example, this allows analyzing functions of the protein, such as which sugar chain will be more firmly bound to the protein.

Further, the sugar chain-immobilized magnetic metal nano-particle may be applied to an interaction detecting agent for detecting interaction between sugar chain and protein, a virus concentrating agent, a cell marker, a magnetic hyperthermia agent, an MRI contrast medium, a diagnostic agent for detecting magnetization by a magnetization detector, etc.

(5. Method for Concentrating Cells or Bacteria)

A method of the present invention for concentrating cells or bacteria includes the step of applying a magnetic force to a mixture containing (i) protein-sugar chain-immobilized magnetic metal nano-particles each having a structure in which a protein is immobilized onto a sugar chain-immobilized magnetic metal nano-particle, (ii) second magnetic particles whose mean particle size is larger than that of the protein-sugar chain-immobilized magnetic metal nano-particles, and (iii) a specimen, the sugar chain-immobilized magnetic metal nano-particle having a structure in which a sugar chain-immobilized metal nano-particle is bound to a first magnetic nano-particle, the sugar chain-immobilized metal nano-particle having a structure in which a ligand-conjugate is bound to a metal nano-particle via sulfur atoms, the ligand-conjugate having a structure in which an amino group of a linker compound is connected to a sugar chain having a reducing terminal, and the linker compound including, in molecules thereof, an amino group, a sulfur atom, and a hydrocarbon chain having a carbon-nitrogen bond.

In the present specification, "protein-sugar chain-immobilized magnetic metal nano-particles" indicate nano-particles having a structure in which a protein is immobilized onto a sugar chain-immobilized magnetic metal nano-particle. The mean particle size of the protein-sugar chain-immobilized magnetic metal nano-particle is not particularly limited as long as the mean particle size is on the nano scale order (more than 0 nm and less than 1 μm) and smaller than mean particle size of the second magnetic particles. The mean particle size of the protein-sugar chain-immobilized magnetic metal nano-particle is preferably not less than 1 nm and less than 100 nm, and more preferably not less than 2 nm and not more than 50 nm.

The sugar chain-immobilized magnetic metal nano-particle may be one already explained above. The first magnetic nano-particle and the second magnetic particle may be ones already explained above. The mean particle sizes of the first magnetic nano-particle and the second magnetic particle have been already explained above.

In the protein-sugar chain-immobilized magnetic metal nano-particles, not only proteins but also sugar chains are immobilized. Sugar chains are immobilized because immobilizing proteins to magnetic metal nano-particles to which sugar chains are not immobilized causes aggregation of magnetic metal nano-particles due to hydrophobicity of proteins. Immobilizing both sugar chains and proteins allows magnetic metal nano-particles to have higher hydrophilicity, thereby increasing diffusibility of the magnetic metal nano-particles in water. Thus, the protein-sugar chain-immobilized magnetic metal nano-particles exhibit excellent diffusibility in water.

Examples of the proteins include an antibody, lectin, a growth factor, and cytokine. Among them, a preferable example is an antibody. The antibody is not particularly limited and may be any conventional and publicly known antibody. For example, anti-CD14 antibody and IgG1 may be preferably used. The lectin is not particularly limited and conventional and publicly known lectins such as concanavalin A and common bean lectin (PHA) may be preferably used.

The protein may be bound to a metal contained in the sugar chain-immobilized magnetic metal nano-particles via a linker compound including thioctic acid part, an oligoethylene oxide group, and a carboxylic acid part (hereinafter referred to as "second linker compound"). An example of the second linker compound is a conventional and publicly known compound represented by general formula (9) below. In particular, a compound whose number of an ethyleneoxide group is four is preferable.

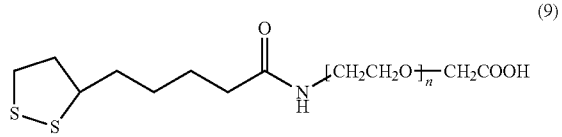

(9)

wherein n is an integer which is not less than 2 and not more than 10).

The second linker compound can bind to a metal contained in the sugar chain-immobilized magnetic metal nano-particles via a sulfur atom contained in the thioctic acid part and can bind to a protein via the carboxylic acid part.

The protein-sugar chain-immobilized magnetic metal nano-particles may be prepared by mixing proteins with sugar chain-immobilized magnetic metal nano-particles. The amount of proteins to be used with respect to the sugar chain-immobilized magnetic metal nano-particles ranges preferably from 1/1000 to 1/100000 (molar ratio), and more preferably from 1/5000 to 1/10000 (molar ratio) with respect to metal atoms contained in the sugar chain-immobilized magnetic metal nano-particles.

Further, the amount of the second linker compound to be used ranges preferably from 1/2 to 1/100 (molar ratio), and more preferably from 1/10 to 1/20 (molar ratio) with respect to a ligand conjugate contained in the sugar chain-immobilized magnetic metal nano-particles.

It is considered that since a magnetic force is applied to the protein-sugar chain-immobilized magnetic metal nano-particles in the presence of the second magnetic particles, the protein-sugar chain-immobilized magnetic metal nano-particles have a magnetic force large enough to overcome the Brownian movement, similarly in the (1. Method for concentrating viruses), thereby allowing efficiently concentrating cells or bacteria.

The specimen is not particularly limited as long as the specimen is capable of contacting the protein-sugar chain-immobilized magnetic metal nano-particles. For example, the specimen may be the same as that in (1. Method for concentrating viruses) such as saliva and nasal mucosa. When proteins capable of binding to surface antigen etc. of cells or bacteria to be concentrated are immobilized to protein-sugar chain-immobilized magnetic metal nano-particles, if the specimen contains the cells or the bacteria, the proteins specifically bind to the cells or the bacteria. Examples of the cells or the bacteria include mononuclear cells, dendritic cells, macrophage, *Escherichia coli*, *Helicobacter pylori*, *Pseudomonas aeruginosa*, Lactic acid bacteria, and *Streptococcus*.

It is preferable that the weight ratio of the protein-sugar chain-immobilized magnetic metal nano-particle to the second magnetic particle is in a range of $1:1\times10^3$ to $1:1\times10^{11}$, similarly with (1. Method for concentrating viruses). Application of a magnetic force is the same as that in (1. Method for concentrating viruses).

A method for confirming the result of concentrating cells or bacteria by the method of the present invention is not particularly limited, and may be a conventional and publicly known method. Examples of the method for confirmation include a method for dyeing collected cells and counting the number of dyed cells under observation by a microscope and a method for diluting and culturing collected cells and counting the number of colonies.

(6. Magnetic Composite)

As long as a magnetic composite containing the protein-sugar chain-immobilized magnetic metal nano-particles and second magnetic particles whose mean particle size is larger than that of the protein-sugar chain-immobilized magnetic metal nano-particles is designed such that proteins capable of binding to surface antigens etc. on cells or bacteria to be concentrated are immobilized to the protein-sugar chain-immobilized magnetic metal nano-particles, mixing the magnetic composite with a specimen allows cells or bacteria in the specimen to bind to the proteins. Since the magnetic composite contains the second magnetic particles, application of a magnetic force to the magnetic composite after the binding allows the cells or the bacteria to be concentrated.

The "protein-sugar chain-immobilized magnetic metal nano-particles" and the "protein" have been already explained above. The magnetic composite can be prepared by, for example, mixing a liquid containing the protein-sugar chain-immobilized magnetic metal nanoparticles with the second magnetic particles. In this case, it is preferable that the weight ratio of the protein-sugar chain-immobilized magnetic metal nano-particle to the second magnetic particle is in a range of $1:1\times10^3$ to $1:1\times10^{11}$.

The present invention may be described as follows.

It is preferable to arrange the method of the present invention such that the mixture is obtained by causing the specimen to contact with the sugar chain of the sugar chain-immobilized magnetic metal nano-particles so as to obtain specimen-contacted magnetic metal nano-particles and thereafter mixing the specimen-contacted magnetic metal nano-particles with the second magnetic particles.

When viruses exist in the specimen, mixing of the sugar chain-immobilized magnetic metal nano-particles, the second magnetic particles, and the specimen allows viruses to recognize sugar chains of the sugar chain-immobilized magnetic metal nano-particles, and the viruses get specifically bound to the sugar chains. Since the viruses do not get bound to the second magnetic particles, binding of the viruses to the sugar chains might be carried out in the presence of the second magnetic particles. However, initially binding viruses to the sugar chains and thereafter mixing the second magnetic particles is more preferable since this case allows prompter and shorter-time binding of viruses to the sugar chains.

It is preferable to arrange the method of the present invention such that the mean particle size of the sugar chain-immobilized magnetic metal nano-particles is not less than 1 nm and less than 100 nm and the mean particle size of the second magnetic bodies is not less than 100 nm and not more than 100 μm.

With the arrangement, the mean particle size of the sugar chain-immobilized magnetic metal nano-particles and the mean particle size of the second magnetic particles are optimal with respect to the size of virus. This further facilitates collection by a magnetic force of the mixture to which virus is bound. This allows prompter, simpler, and higher-sensitive detection and identification of virus.

It is preferable to arrange the method of the present invention such that a weight ratio of the sugar chain-immobilized magnetic metal nano-particles to the second magnetic particles is in a range of $1:1\times10^3$ to $1:1\times10^{11}$.

With the arrangement, a ratio in used amount between the sugar chain-immobilized magnetic metal nano-particles and the second magnetic particles is set to be optimal for collecting by a magnetic force the mixture to which virus is bound. Accordingly, it is possible to carry out prompt, easy, and highly sensitive detection and identification of viruses.

It is preferable to arrange the method of the present invention such that the first magnetic nano-particles and the second magnetic particles are independently selected from iron oxide, magnetite, and ferrite.

Iron oxide, magnetite, and ferrite allow easily depositing a metal on a surface. Therefore, with the arrangement, it is possible to firmly and easily bind the sugar chain-immobilized metal nano-particles to the surface. That is, it is possible to firmly and easily bind sugar chain molecules to the surface via the linker compound. Consequently, when a magnetic force is applied, it is possible to effectively concentrate viruses bound to the sugar chain molecules.

A concentrating device of the present invention includes at least a magnetic composite of the present invention and a magnet.

With the arrangement, when viruses etc. to be concentrated are supplied to the device and bound to the magnetic composite and a magnetic force is applied thereto by a magnet, it is possible to concentrate the viruses etc. This concentration can be performed automatically. This allows prompt, easy, and highly sensitive detection and identification of viruses.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

The following more specifically explains the present invention with reference to these Examples. It should be noted that the present invention is not limited to these Examples.

Example 1

Concentration of Influenza Virus According to the Method of the Present Invention 50 µl of 50 mM iron (II) chloride aqueous solution and 25 µl of 50 mM iron (III) chloride aqueous solution were mixed with each other. 250 µl of 1 M ammonia water was added to the mixture while stirring the mixture. Thus, a solution containing iron oxide magnetic nano-particles serving as a first magnetic nano-particle were prepared.

Subsequently, 75 µl of 50 mM chloroauric acid (III) aqueous solution, 150 µl aqueous solution obtained by adding 5 mg of "ligand-conjugate containing heparin" to sterilized water, and 300 µl of 125 mM sodium borohydride aqueous solution were added to the solution containing iron oxide magnetic nano-particles and the resultant was stirred. Thus, a solution 1 of sugar chain-immobilized magnetic gold nano-particles in which heparin was immobilized (which may be referred to as "heparin-immobilized magnetic gold nano-particles. Mean particle size 33 nm) were prepared.

The "ligand-conjugate containing heparin" was prepared by adding acetic acid to an aqueous heparin solution and N,N-dimethyl acetamide (DMAC) solution (hereinafter referred to as "DMAC solution") in which a linker compound represented by the general formula (3) ($n^1=0$, $q=0$) was dissolved, and then mixing the aqueous heparin solution to which acetic acid was added, the DMAC solution to which acetic acid was added, and $NaBH_3CN$ were mixed in such a manner that a molar ratio among heparin, the linker compound, and $NaBH_3CN$ is 1:1:10, and the mixture was stirred at 37° C. for 3 days.

10 µl of the solution 1 was added to 490 µl of an influenza virus diluted solution in which influenza A virus (A/OKUDA/1957, H2N2) was diluted with PBS to be in an amount of 0.5 HAU/ml and thus a solution 2 was prepared. The solution 2 was left for 30 minutes at a room temperature (25.5° C.).

Subsequently, 10 μl of Dynabeads M-270 30 mg/ml with mean particle size of 2.8 μm (hereinafter merely referred to as "Dynabeads M-270, manufactured by Invitrogen Dynal, product number; DB14305), serving as a second magnetic particle, were added to the solution 2 and left for 30 minutes. As a control, there was provided a trial in which the second magnetic particle is not added and the solution 2 was subjected to the process below. In the specification, sterilized water was prepared by autoclave-sterilizing ion exchange water.

The Dynabeads M-270 was ferrite. "Dynabeads M-270 30 mg/ml" indicates that in a solution containing Dynabeads M-270, the concentration of Dynabeads M-270 was 30 mg/ml.

FIG. 2 is a drawing showing how to apply a magnetic force to the solution 2 containing the second magnetic particle. Magnets (manufactured by Sangyo Supply Co. Ltd., neodymium magnet, surface magnetic flux density; 150 millitesla, 80×15×3 mm) were provided in such a manner as to sandwich a vessel containing the solution 2, and the vessel was shaken up and down 30 times at a velocity of one shaking per 2 sec (i.e. 30 shaking up and down, 1 min in total), so that a magnetic force was applied to a mixture containing sugar chain-immobilized magnetic gold nano-particles in which heparin was immobilized, the second magnetic particle, and influenza virus. Lastly, the magnet was provided at the bottom of the vessel for 2 min so as to completely precipitate the mixture, and thus supernatant and precipitate were obtained. 10 μl of ultrapure water was added to the precipitate and heated at 100° C. for 5 min, and then the magnet was provided at the side of the bottom of the vessel so that a magnetic force was applied for 2 min. Thus, supernatant was obtained.

In a trial to which the second magnetic particle was not added, a magnetic force was applied in the same manner as in the case of adding the second magnetic particle except where the second magnetic particle was not added to the solution 2. Thus, supernatant and precipitate were obtained. Further, in the trial to which the second magnetic particle was not added, there was also provided a trial where the solution 2 was subjected to centrifugation of 10000 G for 2 min, instead of applying a magnetic force. Thus, supernatant and precipitate were obtained. To the precipitate was added 10 μl of ultrapure water, and the resultant was heated at 100° C. for 5 min, and then subjected to centrifugation of 10000 G for 2 min. Thus, supernatant was obtained.

FIG. 1 is a flow chart showing the processes from preparation of the solution 2 to preparation of supernatant supplied to a real time RT-PCR.

2 µl of these supernatants were added to 20 µl of PCR reagent prepared by mixing the reagents shown in Table 1 with respective amounts shown in Table 1, and the resultants were supplied to the real time RT-PCR. Light cycler (trademark, product number 350S, manufactured by Roche) was used as a real time RT-PCR device and SYBR Green was used as a fluorochrome. Primers used here were TypeA/M30F TTCTAACCGAGGTCGAAACG (20 bp, SEQ NO. 1, produced by NIHON GENE RESEARCH LABORATORIES Inc.) and TypeA/M264R2 ACAAAGCGTCTACGCTGCAG (20 bp, SEQ NO. 2, produced by NIHON GENE RESEARCH LABORATORIES Inc.) that are TypeA/M gene-detecting primers described in "Avian influenza (revised on June, 2006)", a pathogen examination manual published by NATIONAL INSTITUTE OF INFECTIOUS DISEASES. With the primers, an M protein region 234 bp of RNA of influenza A virus was amplified. Conditions for RT-PCR were such that reverse transcription reaction was carried out at 45° C. for 2 min, initial thermal degeneration process was carried out at 95° C. for 1 min, and PCR cycle was set 40 cycles with 1 cycle consisting of 95° C. 1 sec, 60° C. 1 sec, and 72° C. 5 sec.

In Table 1, 10×FBI indicates a buffer, and "1×" in the section of the final concentration indicates that 10×FBI is used with 10-time dilution so that 10×FBI becomes "1×" in the section of the final concentration. Further, "1/2000" in the section of the concentration of SYBR Green and "1/20000" in the section of the final concentration indicates that an undiluted solution of TaKaRa 50513 is diluted 2000 times with sterilized water and the diluted solution is used so that the final concentration is 1/20000 of the concentration of the undiluted solution. Further, Prime Script and Speed STAR are enzymes for PCR.

TABLE 1

| Reagent | Concentration | Amount (µl) | Final concentration | Maker, Product name |
|---|---|---|---|---|
| Sterilized water | | 11.3 | — | — |
| 10 × FBI | | 2.0 | 1× | TaKaRa (attached to SpeedSTAR) |
| 2.5 mM dNTPs | | 1.60 | | TaKaRa (attached to SpeedSTAR) |
| M30F primer | 10 µM | 0.5 | 0.25 µM | NIHON GENE RESEARCH LABORATORIES INC. |
| M264R2 primer | 10 µM | 0.5 | 0.25 µM | NIHON GENE RESEARCH LABORATORIES INC. |
| Primer Script | 100 U/µl | 0.65 | 65 U | TaKaRa RR037A |
| SpeedSTAR | 5 U/µl | 0.4 | 2 U | TaKaRa RR070A |
| SYBR Green 1/2000 | 1/2000 | 2.0 | 1/20000 | TaKaRa 50513 |
| Sample | | 1.0 | | |
| Total | | 20.0 | | |

Ct value of 0.5 HAU/ml influenza A virus diluted solution (described as "Ct value before concentration" in Table 2) and Ct value of the supernatant (described as "Ct value after concentration" in Table 2) were measured, and the difference between the Ct values was calculated. As the difference is larger, concentration efficiency is higher. The result is shown in Table 2.

TABLE 2

| | Ct value before concentration (1) | Ct value after concentration (2) | (1) − (2) |
|---|---|---|---|
| Dynabeads M-270 | 24.66 | 21.59 | 3.07 |
| Second magnetic particle unused/magnet | 24.66 | 22.98 | 1.68 |
| Second magnetic particle unused/centrifugation | 24.66 | 21.71 | 2.95 |

In Table 2, a trial labeled as "second magnetic particle unused/magnet" is a trial where the solution 2 was subjected to concentration using a magnet without adding the second magnetic particle to the solution 2. A trial labeled as "second magnetic particle unused/centrifugation" is a trial where the solution 2 was subjected to concentration using centrifugation without adding the second magnetic particle. As shown in Table 2, when the second magnetic particle was not used, the concentration using centrifugation exhibited that the difference between Ct value before concentration and Ct value after concentration was 2.95, whereas the concentration using only a magnet exhibited that the difference was 1.68. This shows that the concentration using only a magnet without using the second magnetic particles exhibited lower concentration efficiency than the concentration using centrifugation. Further, a long time, approximately 30 min, elapsed from a time when a magnetic force was applied to a mixture containing sugar chain-immobilized magnetic gold nano-particles in which heparin was immobilized and influenza virus to a time when precipitate was obtained. On the other hand, when Dynabeads M-270 was used as the second magnetic particle, the difference was 3.07, and concentration efficiency in this case substantially equal to the concentration using centrifugation at 10000 G for 2 min.

Example 2

Analysis of Second Magnetic Particle

Subsequently, it was examined what magnetic particle could be used as the second magnetic particle. Table 3 shows examined magnetic particles.

0981S2453 TS-3 (produced by Powdertech Co., Ltd., referred to as "TS-3" in Table 3 and the following descriptions) is so-called Mn ferrite prepared by adding Mn to magnetite.

Dynabeads M-270 has been already explained in Example 1.

"Dynabeads MyOne 10 mg/ml (merely referred to as "Dynabeads MyOne" in Table 3 and the following descriptions, produced by Invitrogen Dynal, product number; DB65001) indicates that concentration of Dynabeads MyOne when Dynabeads MyOne is added to PBS (pH7.4) containing 0.01% Tween-20 and 0.09% NaN$_3$ is 10 mg/ml. Dynabeads MyOne is a mixture of iron oxide and magnetite.

ProMag 3 series COOH Surfactant Free (PMC3N) (merely referred to as ProMag 3 series in Table 3 and the following descriptions, produced by Bangs Laboratories, Inc., product number; PMC3N) is a magnetic particle (ferrite) similar to Dynabeads M-270, and does not contain a surfactant. ProMag 3 series was used in the form of a suspension liquid in which ProMag 3 series was in an amount of 1.9 g/ml with respect to ion exchange water.

TABLE 3

| Magnetic particle | Mean particle size (μm) | Ct value before concentration (1) | Ct value after concentration (2) | (1) − (2) | Concentration efficiency |
|---|---|---|---|---|---|
| TS-3 | 80 | 28.52 | 24.46 | 4.06 | 17 times |
| Dynabeads M-270 | 2.8 | 28.52 | 23.30 | 5.22 | 37 times |
| Dynabeads My One | 1.0 | 28.52 | 24.51 | 4.01 | 16 times |
| Pro Mag 3 series | 3.1 | 28.52 | 25.21 | 3.31 | 10 times |

There was prepared 490 μl of an influenza virus diluted solution in which influenza A virus (A/OKUDA/1957, H2N2) was diluted with PBS to be in an amount of 0.1 HAU/ml. To the influenza virus diluted solution was added 10 μl of the solution 1 used in Example 1, and thus a solution 2' was obtained. At a room temperature (25.5° C.), the solution 2' (500 μl) was pipetted 10 times at a ratio of 1 pipette/sec, and then further pipetted for 5 min at a ratio of 1 pipette/sec. Pipetting promotes binding of virus to sugar chain of sugar chain-immobilized magnetic metal nano-particles.

Subsequently, to the solution 2' (500 μl) was added one of 10 μl of a liquid obtained by suspending 20 mg of TS-3 in 2 ml of sterilized water, 10 μl of Dynabeads M-270, 10 μl of Dynabeads MyOne, and 10 μl of ProMag 3 series. The resultant was pipetted 10 times at a ratio of 1 pipette/sec.

Subsequently, as shown in FIG. 2, magnets (manufactured by Sangyo Supply Co. Ltd., neodymium magnet, surface inductive flux; 150 millitesla, 80×15×3 mm) were provided in such a manner as to sandwich a vessel containing the solution 2' to which the magnetic particle shown in Table 3 was added. The vessel was shaken up and down 30 times at a velocity of one shaking per 2 sec (i.e. 30 shaking up and down, 1 min in total), so that a magnetic force was applied to a mixture containing heparin-immobilized magnetic gold nano-particles in which heparin was immobilized, the magnetic particle shown in Table 3, and influenza virus. Lastly, the magnet was provided at the bottom of the vessel for 1 min so as to completely precipitate the mixture, and thus supernatant and precipitate were obtained.

10 μl of sterilized water was added to the precipitate, and the resultant was pipetted 10 times and heated at 100° C. for 2 min, and then a magnetic force was applied to the resultant by the magnet for 2 min, so that supernatant was obtained. 2 μl of the obtained supernatants was subjected to real time RT-PCR under the same conditions as those in Example 1. Ct value of 0.1 HAU/ml influenza A virus diluted solution (described as "Ct value before concentration" in Table 3) and Ct value of the supernatant (described as "Ct value after concentration" in Table 3) were measured, and the difference between the Ct values were calculated.

As shown in Table 3, in the case of using Dynabeads M-270, the difference was 5.22. That is, compared with the case of subjecting a 0.1 HAU/ml influenza A virus (A/OKUDA/1957, H2N2) diluted solution to RT-PCR without concentrating the solution, use of Dynabeads M-270 allows detection of virus faster by 5.22 cycle, and consequently concentration efficiency was increased by $2^{5.22}=37$ times. In later-mentioned Comparative Example 1, a colloid solution (10 μl) of heparin-immobilized gold nano-particles (mean particle size; 15 nm) was mixed with the influenza virus diluted solution (490 μl), and the resultant was subjected to centrifugation (10000 G, 10 min) so as to obtain precipitate, and 10 μl of ultrapure water was added to the precipitation, and the resultant was heated at 100° C. for 5 min, and then subjected to centrifugation at 10000 G for 10 min so as to obtain supernatant. The difference between Ct value of the supernatant and Ct value of 0.1 HAU/ml influenza A virus diluted solution was calculated (5.37). Since the difference 5.22 obtained in the case of using Dynabeads M-270 is almost equal to 5.37, it is found that use of Dynabeads M-270 exhibited substantially the same concentration efficiency as the case of using centrifugation.

In the cases of using TS-3, Dynabeads MyOne, and Pro Mag 3 series, these cases exhibited lower concentration efficiency than the case of using Dynabeads M-270. However, as shown in Table 3, these cases exhibited concentration efficiency 10 times or more greater than the case of subjecting the influenza A virus diluted solution to RT-PCR without concentrating the solution. These results were superior to concentration efficiency in later-mentioned Comparative Example 1 in which 0.1 HAU/ml influenza A virus was concentrated using only sugar chain-immobilized magnetic metal nano-particles without using the second magnetic particles (2 times and 8 times in later-mentioned Table 4). Therefore, also in the cases of using TS-3, Dynabeads My One, and Pro Mag 3 series, it is possible to increase concentration efficiency while avoiding dangers such as dispersion of a sample seen when concentration is performed with centrifugation, compared with the case of using only sugar chain-immobilized magnetic metal nano-particles. Accordingly, the present invention is useful.

Example 3

Preparation of α-Glucose-Immobilized Magnetic Metal Nano-Particles

50 μl of 50 mM iron (II) chloride aqueous solution and 25 μl of 50 mM iron (III) chloride aqueous solution were mixed with each other. 250 μl of 1 M ammonia water was added to the mixture while stirring the mixture. Thus, a solution containing iron oxide magnetic nano-particles serving as a first magnetic particle were prepared. Subsequently, 75 μl of 50 mM chloroauric acid (III) aqueous solution, 150 μl of an ligand-conjugate aqueous solution (concentration 10 mM), and 300 μl of 125 mM sodium borohydride were added to the solution containing iron oxide magnetic nano-particles and the resultant was stirred. Thus, a colloid solution of crude α-glucose-immobilized magnetic gold nano-particles was prepared. The ligand-conjugate was prepared by dissolving 20 mg of maltose and 19 mg of the linker compound represented by the general formula (3) ($n^1=0$, q=0) in 5.5 ml of a mixture in which water, N,N-dimethylacetamide, and acetate were mixed in a ratio of 10:10:1, and then the resultant was subjected to reductive amination.

Subsequently, the colloid solution of the crude α-glucose-immobilized magnetic gold nano-particles was refined by supercentrifugation (50000 G, 20 min) and magnetic separation using a neodymium magnet so as to obtain a colloid solution of α-glucose-immobilized magnetic gold nano-particles. "Magnetic separation using a neodymium magnet" indicates that a magnet (KENIS LIMITED, magnet bar with high magnetic force, surface inductive flux: 1.2 tesla at maximum, 25Φ×100 mm) was caused to contact with the bottom of a vessel containing a colloid solution of the crude α-glucose-immobilized magnetic gold nano-particles, supernatant was removed from the solution so as to refine crude α-glucose-immobilized magnetic gold nano-particles, so that a colloid solution of α-glucose-immobilized magnetic gold nano-particles was obtained.

Figure 3:
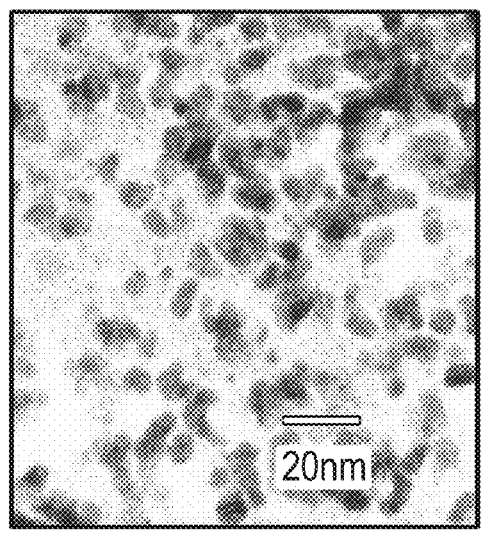
FIG. 3 is a drawing showing a picture, captured by a transmission electron microscope, of a colloid solution of crude α-glucose-immobilized magnetic gold nano-particles.

FIG. 3 shows a picture, captured by a transmission electron microscope, of the colloid solution of the prepared crude α-glucose-immobilized magnetic gold nano-particles.

Example 4

Collection of ConA from Protein-Sugar Chain Interacting Particle Precipitate

100 µl of a ConA solution in which 1.24 mg/ml of ConA was dissolved in PBS-T and 100 µl of a BSA solution in which 1.0 mg/ml of BSA was dissolved in PBS-T were dispensed in an Eppendorf tube. To the resultant was added 100 µl of the colloid solution of α-glucose-immobilized magnetic gold nano-particles prepared in Example 3, and the resultant was stirred 10 sec or more by a vortex mixer. PBS-T is a solution obtained by adding, to a phosphate buffer, Tween 20 that is 0.05% detergent. The resultant was left for approximately 2 hours, and then a protein-sugar chain interacting particle precipitate was obtained by magnetic separation using a neodymium magnet as in Example 3, and supernatant was collected, and the protein-sugar chain interacting particle precipitate was washed several times with PBS-T and water. After the washing, 100 µl of a 4 mg/ml glucose solution was added to the protein-sugar chain interacting particle precipitate, which was left for approximately 1 hour. ConA dissociated from the protein-sugar chain interacting body was evaluated by SDS-PAGE analysis.

Figure 4:
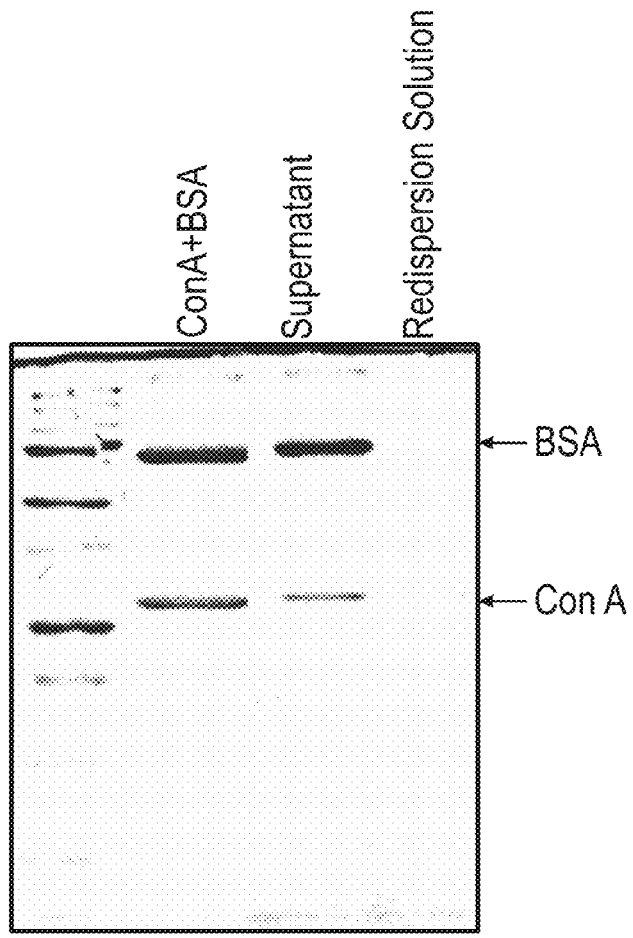
FIG. 4 is a drawing showing a picture of the process of refining protein in SDS-PAGE analysis.

FIG. 4 shows a picture of the process of refining protein in SDS-PAGE analysis. Images in the picture show, from the left, marker protein, a solution before addition of α-glucose-immobilized magnetic gold nano-particles, supernatant after addition of α-glucose-immobilized magnetic gold nano-particles, and a solution after disassociation of a protein-sugar chain interacting particle precipitate, respectively.

Comparative Example 1

As shown in Example 1, in the case of using only sugar chain-immobilized magnetic metal nano-particles without the second magnetic particle, applying only a magnetic force did not exhibited concentration efficiency almost equal to that in the case of centrifugation. Therefore, the inventors of the present invention examined whether it was possible to solve this problem by enlarging the particle size of the sugar chain-immobilized magnetic metal nano-particles without using the second magnetic particle.

Gold/iron oxide magnetic complex nano-particles (produced by ACT NONPAREIL, Lot No. 090711Rv) were used as the sugar chain-immobilized magnetic metal nano-particles. The gold/iron oxide magnetic complex nano-particles are nano-particles whose cores are made of iron oxide ($Fe_3O_4$) with mean particle size of 30 nm. The surface of the nano-particle is coated with PVP (polyvinyl pyrrolidone, water-soluble polymer). The nano-particle contains 3.62 mg/ml of $Fe_3O_4$ and 2.24 mg/ml of Au. The gold/iron oxide magnetic complex nano-particles were synthesized by emitting an electron beam to a dispersed solution obtained by dispersing iron oxide in an aqueous solution containing gold ions and PVP.

Observation of the gold/iron oxide magnetic complex nano-particles by a transmission electron microscope showed that each particle was amorphous particle with long axis of approximately 200 nm and short axis of approximately 50 nm. Therefore, mean particle size of the gold/iron oxide magnetic complex nano-particles was larger than that of the heparin-immobilized magnetic gold nano-particles (mean particle size: 33 nm).

250 µl of a liquid obtained by adding the gold/iron oxide magnetic complex nano-particles to water so that the gold/iron oxide magnetic complex nano-particles were in amounts of 6 mg/ml was mixed with 245 µl of an aqueous solution of a ligand-conjugate (100 mg/ml) containing heparin so as to prepare a colloid solution of heparin-immobilized gold/iron oxide magnetic complex nano-particles. The "ligand-conjugate containing heparin" was prepared in the same manner as in Example 1.

To an influenza virus diluted solution (490 µl) in which influenza A virus (A/OKUDA/1957, H2N2) was diluted with PBS so that the virus in an amount of 0.1 HAU/ml was mixed with a colloid solution (10 µl) of heparin-immobilized gold/iron oxide magnetic complex nano-particles, and the mixture was stirred at 4° C. for 30 min to obtain a solution. A magnet (manufactured by Sangyo Supply Co. Ltd., neodymium magnet, surface inductive flux; 150 millitesla, 80×15×3 mm) was provided under a tube containing the obtained solution, and a magnetic force was applied to the tube for 10 sec or 30 sec, so as to precipitate a complex of the heparin-immobilized gold/iron oxide magnetic complex nano-particles and the virus. Supernatant was removed, and 10 µl of ultrapure water was added to the precipitation of the complex, and the resultant was heated at 100° C. for 10 min, and the magnet was provided at the bottom of the vessel and a magnetic force was applied for 2 min, and thus supernatant was obtained.

As a control, instead of the colloid solution (10 µl) of heparin-immobilized gold/iron oxide magnetic complex nano-particles, a colloid solution (10 µl) of heparin-immobilized gold nano-particles (mean particle size; 15 nm) was mixed with the influenza virus diluted solution (490 µl), and the resultant was subjected to centrifugation (10000 G, 10 min), and supernatant and precipitate were obtained. 10 µl of ultrapure water was added to the precipitate and the resultant was heated at 100° C. for 5 min, and subjected to centrifugation of 10000 G for 10 min, and supernatant was obtained.

The colloid solution of heparin-immobilized goldnano-particles was prepared by mixing a sodium gold (III) chloride aqueous solution whose final concentration was 1 mM, a trisodium citrate dihydrate aqueous solution whose final concentration was 8.1 mM, and the "ligand-conjugate containing heparin" whose final concentration ranges from 200 to 2000 mg/ml and stirring the mixture at 100° C. for 10 min.

2 µl of the supernatant was added to 23 µl of a PCR reagent, and the resultant was subjected to real time RT-PCR. As the reagent, One Step SYBR PrimeScript RT-PCR Kit II (TAKARA BIO INC., product code RR086A) was used. The reagent per one reaction was prepared by mixing 12.5 µl of 2× One Step SYBR RT-PCR Buffer 4, 1 µl of PrimeScript 1 step Enzyme Mix 2, 1 µl of PCR Forward Primer (10 µM), 1 µl of PCR Reverse Primer (10 µM), and 7.5 µl of Rnase Free distilled water. As a real time RT-PCR device, Thermal Cycler Dice Real Time System (product number TP800, manufactured by TAKARA BIO INC.) was used. As a fluorochrome, SYBR Green was used. Primers used here were TypeA/MP gene (217-236) Forward GGACTGCAGCGTAGACGCTT (20 bp, SEQ NO. 3, TSUKUBA OLIGO SERVICE CO., LTD.) and TypeA/MP gene (382-405) Reverse CATYCTGTTGTATATGAGGCCCAT (24 bp, SEQ NO.4, TSUKUBA OLIGO SERVICE CO., LTD.) that were primers for detecting TypeA/MP gene (J. Clin Microbiol. 2005 43 No. 2:589-95.) of influenza virus. With the primers, an M protein region 188 bp of RNA of influenza A virus was amplified. Conditions for RT-PCR were such that reverse transcription reaction was carried out at 45° C. for 5 min, initial thermal degeneration process was carried out at 95° C. for 10 sec, and PCR was carried out 40 cycles with 1 cycle consisting of PCR at 95° C. for 5 sec and PCR at 60° C. for 30 sec.

Ct value of 0.1 HAU/ml influenza A virus diluted solution (described as "Ct value before concentration" in Table 4) and Ct value of the supernatant (described as "Ct value after concentration" in Table 4) were measured, and the difference between the Ct values were calculated. As the difference is larger, concentration efficiency is higher. The result is shown in Table 4.

TABLE 4

|  | Ct value before concentration (1) | Ct value after concentration (2) | (1) − (2) | Concentration efficiency |
| --- | --- | --- | --- | --- |
| 10 sec contact with magnet | 34.83 | 33.61 | 1.22 | 2 times |
| 30 sec contact with magnet | 34.83 | 31.91 | 2.92 | 8 times |
| Centrifugation (10000 G) | 34.83 | 29.46 | 5.37 | 41 times |

In Table 4, "10 sec contact with magnet" indicates the result of using supernatant obtained from a trial where the colloid solution of heparin-immobilized gold/iron oxide magnetic complex nano-particles was used and the neodymium magnet was provided under the tube so as to apply a magnetic force for 10 seconds. "30 sec contact with magnet" indicates the result of using supernatant obtained from a trial where the colloid solution of heparin-immobilized gold/iron oxide magnetic complex nano-particles was used and the neodymium magnet was provided under the tube so as to apply a magnetic force for 30 seconds. "Centrifugation (10000 G)" indicates the result of using supernatant obtained in a case where the colloid solution of heparin-immobilized gold nano-particles (mean particle size: 15 nm) was used.

According to the results, in the case of the colloid solution of heparin-immobilized gold nano-particles, the difference was 5.37. That is, this case allows detecting virus faster by 5.37 cycles than the case where a 0.1 HAU/ml influenza A virus diluted solution was subjected to RT-PCR without concentrating the solution, and concentration efficiency was increased by 25.37=41 times.

On the other hand, in the case of using the colloid solution of heparin-immobilized gold/iron oxide complex nano-particles, although it was possible to precipitate a complex of heparin-immobilized gold/iron oxide complex nano-particles and the virus within one minute, the difference in the case of "10 sec contact with magnet" was 1.22 and the difference in the case of "30 sec contact with magnet" was 2.92. That is, these cases allow detecting virus faster only by 1.22 cycles and 2.92 cycles, respectively, than the case where a 0.1 HAU/ml influenza A virus diluted solution was subjected to RT-PCR without concentrating the solution, and concentration efficiency was increased only by 2 times and 8 times, respectively. As described above, in the case where the particle size of the sugar chain-immobilized magnetic metal nano-particles was enlarged without using the second magnetic particle, it was impossible to obtain concentration efficiency almost equal to that in the case of centrifugation.

Example 5

Preparation of Magnetic Gold Nano-Particles to which Antibody is Immobilized)

50 µl of 50 mM iron (III) chloride aqueous solution and 25 µl of 50 mM iron (II) sulfate aqueous solution were mixed with each other. 1 M $NH_4OH$ was added to the mixture while stirring the mixture, and the resultant was left for 30 min at a room temperature. Thus, a solution containing iron oxide magnetic nano-particles serving as a first magnetic nano-particle were prepared.

75 µl of a 150 mM $HAuCl_4$ aqueous solution was added to the solution and the solution was stirred. Subsequently, 15 µl of a 10 mM linker compound represented by general formula (9) where n=4, 135 µl of a ligand conjugate aqueous solution (concentration 10 mM), and 300 µl of 125 mM sodium borohydride were added to the solution and the solution was stirred, and then left for 6 hours at a room temperature. The ligand conjugate was the same as that prepared in Example 3.

The liquid thus prepared was subjected to 50000 g centrifugation for 20 min, and then supernatant was removed and precipitate was suspended in 1 ml of super pure water. The process from the centrifugation to the suspension was repeated three times, and then the finally obtained precipitate was suspended in 800 µl of super pure water. To 100 µl of the suspension thus obtained was added 100 µl of 0.2 M EDC (1-ethyl-3-(3-dimethylaminopropyl)carbodiimide at 4° C., and then the resultant was put at a room temperature again and stirred for 30 min. Then, supernatant was removed by 50000 g centrifugation for 20 min.

The precipitate was washed using a 50 mM MES buffer solution (pH 5.0). Then, to the precipitate was added 0.1 ml of a MES buffer solution (pH 5.0) to which an antibody protein (mouse anti-human CD14 antibody (Affinity Purified anti-human CD14 (eBioscience □14-0149)) or mouse IgG1 antibody (Affinity Purified Mouse IgG1 Isotype Control (eBioscience □14-4714))) was added in such a manner that the amount of the antibody protein was 0.05 mg/ml. The resultant was stirred for 1 hour at a room temperature, and then supernatant was removed by 50000 g centrifugation for 20 min. 100 µl of 50 mM ethanol amine was added to precipitate and the resultant was stirred for 1 hour at a room temperature, and then subjected to 50000 g centrifugation for 20 min in order to remove supernatant. Precipitate was washed using a 50 mM Tris buffer solution (pH 7.4. Containing 0.1% Tween 20), and then 50 µl of the buffer solution was added to the precipitate and the precipitate was dispersed sufficiently by pipetting.

Thus, a dispersion liquid containing magnetic gold nano-particles to which α-glucose and antibody proteins were immobilized (mean particle size: several ten nm) was prepared. The dispersion liquid is hereinafter referred to as "antibody-immobilized SMGNP".

As a control, there were prepared magnetic particles in the same manner as in preparation of the dispersion liquid containing the antibody-immobilized SMGNP except that Dynabeads M-270 with mean particle size of 2.8 µm, used in Example 1, was used as the first magnetic nano-particle. Thus, magnetic particles in which antibody proteins were immobilized to Dynabeads M-270 were prepared as a control (which are referred to as "antibody-immobilized Dynabeads M-270"). Since the antibody-immobilized Dynabeads M-270 had a strong magnetism, the antibody-immobilized Dynabeads M-270 were subjected to magnetic separation instead of centrifugation performed in preparation of the antibody-immobilized SMGNP.

The magnetic separation was performed in the same manner as in Example 1 and FIG. 2. That is, Magnets (manufactured by Sangyo Supply Co. Ltd., neodymium magnet, surface magnetic flux density; 150 millitesla, 80×15×3 mm) were provided in such a manner as to sandwich a vessel containing the dispersion liquid, and the vessel was shaken up and down 30 times at a velocity of one shaking per 2 sec, so that a magnetic force was applied to the dispersion liquid.

Figure 5:
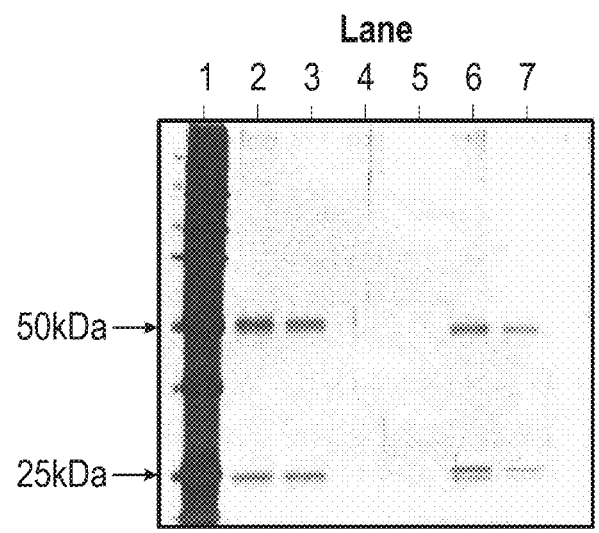
FIG. 5 is a drawing showing the result of SDS-PAGE indicating that antigen proteins are immobilized to α-glucose-immobilized magnetic gold nano-particles and Dynabeads M-270.

Immobilization of the antibody proteins to the antibody-immobilized SMGNP and the antibody-immobilized Dynabeads M-270 was confirmed as follows: 2 ml of a 2×SDS PAGE Sample buffer was added to 2 ml of a suspension liquid of particles to which the antibodies were immobilized, the mixture was heated at 100° C. for 10 min, and then subjected to electrophoresis at 20 mA for 90 min using 10% polyacrylamide gel, and subjected to silver stain. The result is shown in FIG. 5. FIG. 5 shows the result of SDS-PAGE indicating that mouse anti-human CD14 antibodies and mouse IgG1 antibodies were immobilized to the antibody-immobilized SMGNP and the antibody-immobilized Dynabeads M-270.

In FIG. 5, lane 1 indicates molecular mass marker, lane 2 indicates antibody-immobilized SMGNP to which mouse anti-human CD 14 antibodies were immobilized, lane 3 indicates antibody-immobilized SMGNP to which mouse IgG1 antibodies were immobilized, lane 6 indicates antibody-immobilized Dynabeads M-270 to which mouse anti-human CD14 antibodies were immobilized, and lane 7 indicates antibody-immobilized Dynabeads M-270 to which mouse IgG1 antibodies were immobilized.

In each of lanes 2, 3, 6, and 7, bands of heavy chain (50 kDa) and light chain (approximately 25 kDa) of antibodies were observed. This indicates that the antibodies were bound to respective particles.

Example 6

Experiment for Collecting CD14 Positive Monocyte

By magnetically separating CD14 positive cells from a liquid containing monocytes derived from human peripheral blood, it was demonstrated that the antibody-immobilized SMGNP to which mouse anti-human CD14 antibodies were immobilized (nano-particles prepared in Example 5) had a better collecting ability than the antibody-immobilized Dynabeads M-270 which were microparticles.

Specifically, a suspension of monocytes separated from healthy human peripheral blood ($3.8 \times 10^7$ cells/5 ml) was prepared. 500 µl of the suspension ($3.8 \times 10^6$ cells) was subjected to 300 g centrifugation for 10 min at a room temperature, and supernatant of precipitated monocytes was suspended again in 50 µl of PBS. To the suspension was added 20 µl of a dispersion liquid of the antibody-immobilized SMGNP to which the mouse anti-human CD14 antibodies were immobilized or a 20 µl of a dispersion liquid of the antibody-immobilized SMGNP to which the mouse IgG1 antibodies were immobilized. The mixture was pipetted and then left at 4° C. for 30 min. Note that the dispersion liquid was the dispersion liquid prepared in Example 5 containing the antibody-immobilized SMGNP.

Subsequently, 10 µl of Dynabeads M-270 (diluted to ⅕ by PBS to attain concentration of 6 mg/ml), which were second magnetic particles whose mean particle size was larger than that of the antibody-immobilized SMGNP, were added to the suspension liquid, and the suspension liquid was stirred gently, and then left at 4° C. for 15 min. Further, 1 ml of PBS was added to the suspension liquid, and the suspension liquid was stirred gently and then magnets (manufactured by Sangyo Supply Co. Ltd., neodymium magnet, surface magnetic flux density; 150 millitesla, 80×15×3 mm) were provided in such a manner as to sandwich a vessel containing the suspension liquid for 4 min, so as to collect the antibody-immobilized SMGNP, the Dynabeads M-270 (6 mg/ml), and cells bound to the antibody-immobilized SMGNP. Supernatant was removed from the collected particles and cells, and then 100 µl of PBS was added to the resulting particles and cells, which were suspended sufficiently by pipetting, so that a resuspension liquid was prepared. 20 µl of a trypan blue solution was added to 20 µl of the resuspension liquid, and the number of cells was counted under observation by a microscope. As a control, cells were collected in the same manner as above except that the antibody-immobilized Dynabeads M-270 to which the mouse anti-human CD14 antibodies were immobilized or the antibody-immobilized Dynabeads M-270 to which the mouse IgG1 antibodies were immobilized were used, so that the number of the collected cells was counted.

Figure 6:
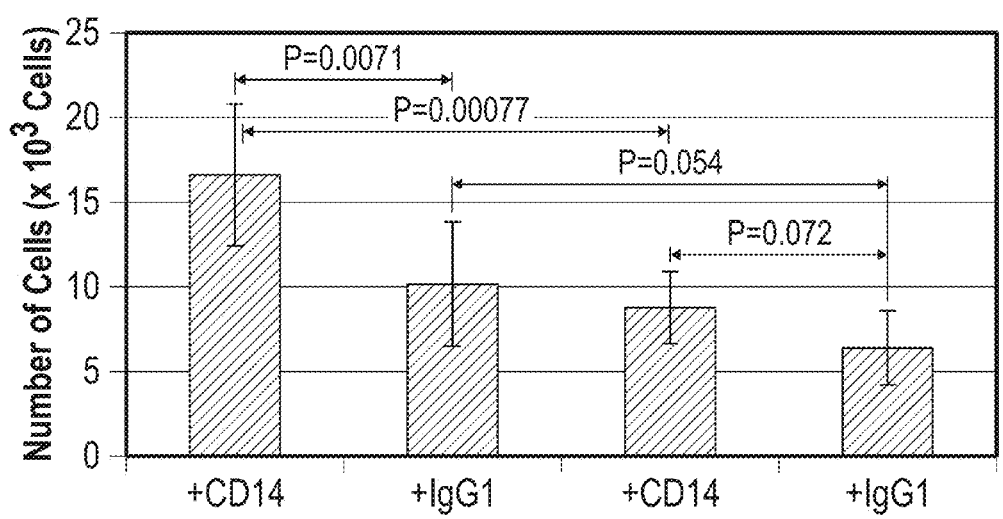
FIG. 6 is a drawing showing the number of cells collected by using antibody-immobilized protein-sugar chain-immobilized magnetic metal nano-particles or antibody-immobilized Dynabeads M-270.

FIG. 6 is a drawing showing the number of cells collected using the antibody-immobilized SMGNP or the antibody-immobilized Dynabeads M-270. On the lateral axis, from left to right, "+CD14" indicates the antibody-immobilized SMGNP to which the mouse anti-human CD14 antibodies were immobilized, "+IgG1" indicates the antibody-immobilized SMGNP to which the mouse IgG1 antibodies were immobilized, "+CD14" indicates the antibody-immobilized Dynabeads M-270 to which the mouse anti-human CD14 antibodies were immobilized, and "+IgG1" indicates the antibody-immobilized Dynabeads M-270 to which the mouse IgG1 antibodies were immobilized. The longitudinal axis indicates the number of cells. It is shown from FIG. 6, with a significant difference of $p<0.01$, that approximately twice the number of cells were collected when using the antibody-immobilized SMGNP to which the mouse anti-human CD14 antibodies were immobilized, compared with when using antibody-immobilized Dynabeads M-270 to which the mouse anti-human CD14 antibodies.

It is shown from the result of FIG. 6 that antibodies immobilized to magnetic gold nano-particles can bind to antigen proteins on the surface of cells more efficiently than antibodies immobilized to Dynabeads M-270 which are magnetic microparticles. Further, as described above, by applying a magnetic force to a mixture containing (i) the antibody-immobilized SMGNP having a structure in which an antibody-immobilized gold nano-particle is bound to a first magnetic nano-particle, (ii) a second magnetic particle (Dynabeads M-270) whose mean particle size was larger than that of the antibody-immobilized SMGNP, and (iii) a specimen, it was possible to efficiently collect cells. This indicates that the method of the present invention using the first magnetic nano-particle and the second magnetic particle is effective also in the case where a target to be concentrated is a cell.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A method comprising:

contacting modified nano-particles with a specimen containing one or more viruses to form virus-bound, modified nano-particles; and mixing the virus-bound, modified nano-particles with magnetic particles to form a mixture comprising virus-bound, modified nano-particles and magnetic particles applying a magnetic force to the mixture comprising virus-bound, modified nano-particles and magnetic particles, wherein applying the magnetic force results in the formation of an accumulation of the virus-bound, modified nano-particles and the magnetic particles;

wherein the mean particle size of the modified nano-particles is not less than 1 nm and less than 100 nm and the mean particle size of the magnetic particles is not less than 100 nm and not more than 100 μm, wherein the virus-bound, modified nano-particles each comprise:

one or more viruses, a metal nano-particle, a magnetic nano-particle bound to the metal nano-particle, and a ligand-conjugate, wherein the ligand-conjugate is bound to the one or more viruses and the ligand-conjugate is bound to the metal nano-particle via one or more sulfur atoms of the ligand-conjugate, wherein the ligand-conjugate comprises:

one or more sugar chains comprising a reducing terminus, and a linker compound comprising one or more amino groups, one or more sulfur atoms, and a hydrocarbon chain having a carbon-nitrogen bond;

wherein the one or more amino groups of the linker compound are independently connected to the reducing terminus of the one or more sugar chains;

wherein:
  when the virus is influenza virus, the one or more sugar chains are each independently selected from the group consisting of: heparin, NeuAcα2-6Galβ1-4GlcNAcβGlc, NeuAcα2-6Galβ1-3GlcNAcβGlc, NeuAcα2-3Galβ1-4GlcNAcβGlc, and NeuAcα2-3Galβ1-3GlcNAcβGlc,
  when the virus is selected from the group consisting of herpes simplex virus, venereal virus, varicella virus (VZV), cytomegalovirus (CMV), lentivirus, koi herpesvirus, and adenovirus, the one or more sugar chains are each independently selected from the group consisting of: heparin, heparan sulfate, disaccharide structures that are found in heparan sulfate, chondroitin sulfate, and disaccharide structures that are found in chondroitin sulfate,
  when the virus is selected from the group consisting of AIDS virus and adult T-cell leukemia virus, the one or more sugar chains are each independently selected from the group consisting of: heparin, heparan sulfate, and disaccharide structures that are found in heparan sulfate,
  when the virus is Noro virus, the one or more sugar chains are each independently selected from the group consisting of: fucose and N-acetylgalactosamine, and
  when the virus is rotavirus, the one or more sugar chains are each lactose;
wherein the linker compound is selected from the group consisting of:
a compound having a structure represented by general formula (1)

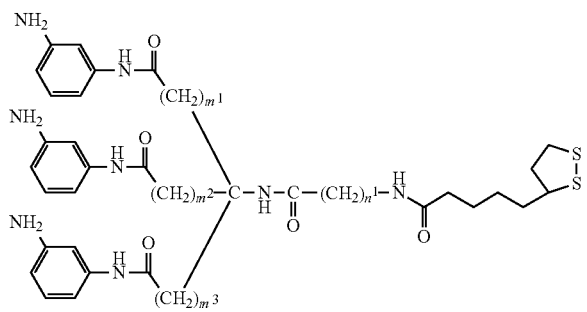

(1)

wherein $m^1$, $m^2$, and $m^3$ independently indicate an integer of 0 to 6, and $n^1$ indicates an integer of 1 to 6;
a compound having a structure represented by general formula (2)

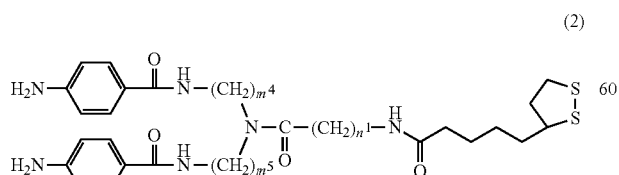

(2)

wherein $m^4$ and $m^5$ independently indicate an integer of 0 to 6, and $n^1$ indicates an integer of 1 to 6;

a compound having a structure represented by general formula (3)

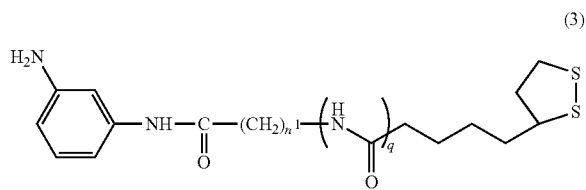

(3)

wherein $n^1$ and q independently indicate an integer of 0 to 6;

a compound having a structure represented by general formula (4)

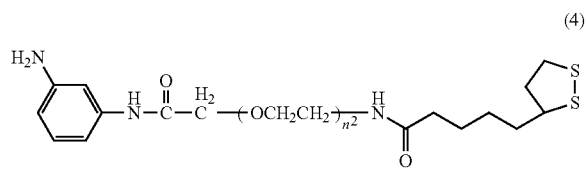

(4)

wherein $n^2$ is an integer of 1 to 6;

a compound having a structure represented by general formula (5)

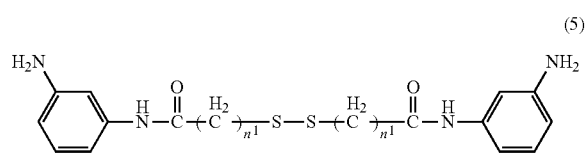

(5)

wherein $n^1$ is an integer of 1 to 6;

a compound having a structure represented by general formula (6)

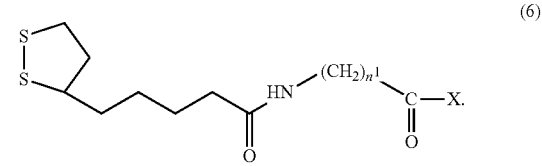

(6)

wherein $n^1$ is an integer of 1 to 6, and X is represented by general formula (7)

(7)

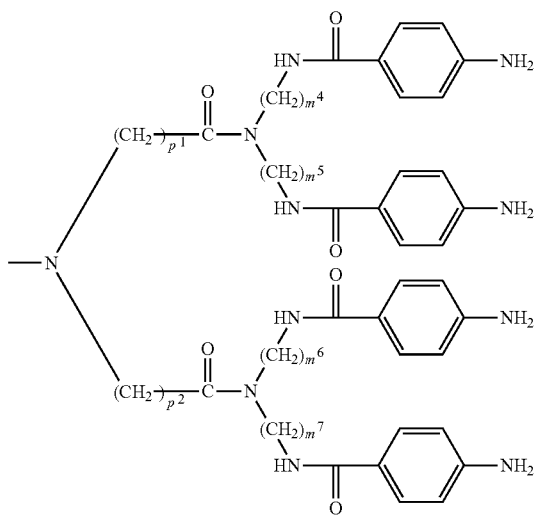

wherein $m^4$, $m^5$, $m^6$, $m^7$, $P^1$, and $P^2$ independently indicate an integer of 1 to 6; and a compound having a structure represented by chemical formula (8)

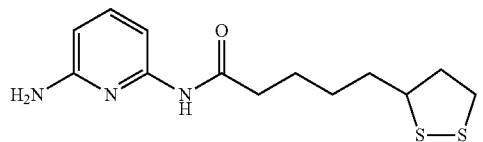

(8)

2. The method of claim 1, wherein a weight ratio of the modified nano-particles to the magnetic particles is in a range of $1:1\times10^3$ to $1:1\times10^{11}$.

3. The method of claim 1, wherein the magnetic nano-particles and the magnetic particles are each independently selected from the group consisting of iron oxide, magnetite, and ferrite.

* * * * *